US006838559B2

(12) United States Patent
Vaccaro et al.

(10) Patent No.: US 6,838,559 B2
(45) Date of Patent: Jan. 4, 2005

(54) PURINE INHIBITORS OF PHOSPHODIESTERASE (PDE) 7

(75) Inventors: Wayne Vaccaro, Yardley, PA (US); Jacques Y. Roberge, Princeton, NJ (US); Katerina Leftheris, Skillman, NJ (US); William J. Pitts, Newtown, PA (US); Joseph Barbosa, Lambertville, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/173,530

(22) Filed: Jun. 17, 2002

(65) Prior Publication Data

US 2003/0100571 A1 May 29, 2003

Related U.S. Application Data

(60) Provisional application No. 60/368,752, filed on Mar. 29, 2002, and provisional application No. 60/299,287, filed on Jun. 19, 2001.

(51) Int. Cl.$^7$ .................. C07D 473/16; C07D 473/24; A61K 31/52; A61K 31/522; A61P 29/00
(52) U.S. Cl. .............. 540/575; 544/118; 544/276; 544/277
(58) Field of Search ................ 544/118, 276, 544/277; 514/263.27, 263.38, 263.21, 263.22, 263.2, 263.4, 234.2

(56) References Cited

U.S. PATENT DOCUMENTS

| | | | |
|---|---|---|---|
| 3,936,439 A | * | 2/1976 | Marumoto et al. ...... 536/27.61 |
| 5,240,938 A | | 8/1993 | Greenlee et al. |
| 5,290,801 A | | 3/1994 | Higley et al. |
| 5,646,155 A | * | 7/1997 | Wright ................ 544/277 |
| 5,792,868 A | | 8/1998 | Izawa et al. |
| 5,869,468 A | | 2/1999 | Freeman |
| 5,889,178 A | * | 3/1999 | Gregson et al. ......... 536/27.22 |
| 6,414,147 B1 | * | 7/2002 | Currie et al. ............. 544/276 |
| 6,426,337 B1 | * | 7/2002 | Cox et al. .................. 514/45 |

FOREIGN PATENT DOCUMENTS

| | | |
|---|---|---|
| DE | 4008858 | 9/1991 |
| EP | 467207 | 1/1992 |
| EP | 513979 | 11/1992 |
| EP | 544445 | 6/1993 |
| EP | 617046 | 9/1994 |
| EP | 624372 | 11/1994 |
| EP | 728757 | 8/1996 |
| EP | 827960 | 3/1998 |
| EP | 532878 | 6/1999 |
| EP | 1043324 | 10/2000 |
| GB | 2276383 | 9/1994 |
| JP | 775798 | 3/1995 |
| WO | WO 93/17021 | 9/1993 |
| WO | WO 94/10171 | 5/1994 |
| WO | WO 95/26734 | 10/1995 |
| WO | WO 97/16452 | 5/1997 |
| WO | WO 97/35539 | 10/1997 |
| WO | WO 98/07725 | 2/1998 |
| WO | WO 00/68230 | 11/2000 |

OTHER PUBLICATIONS

Roberts, "Basic Principles of Organic Chemistry", p. 99–100.*
"Basic Organic Nomenclature" http://www.shsu.edu/~chm_bea/BON.doc downloaded from the internet Feb. 18, 2004.*
Crute, J. Med. Chem 38, 1820 (1995).*
Wright, J. Med Chem 30, 109–116, 1987.*
Gardner, Biochemical and Biophysical Research Communications 272, 186 (2000).*
Schow et al., Bioorganic & Medicinal Chemistry Letters, 7(21):2697–2702 (1997).
Moharram et al., Egypt. J. Pharm. Sci., 31 (1–4):487–494 (1990).
Vesely et al., Eur. J. Biochem., 224:771–786 (1994).
De Azevedo et al., Eur. J. Biochem., 243:518–526 (1997).
Letham et al., Phytochemistry, 17:2053–2057 (1978).
Parker et al., Phytochemistry, 25(2): 303–310 (1986).
Nakata A. et al., Clin. Exp. Immunol. 2002, vol. 128, pp. 460–466.

* cited by examiner

Primary Examiner—Mark L. Berch
(74) Attorney, Agent, or Firm—Laurelee A. Duncan

(57) ABSTRACT

Purine phosphodiesterase 7 (PDE 7) inhibitors of the following formulas

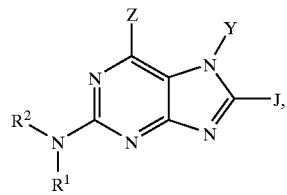

Ia

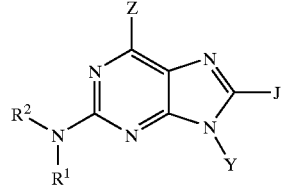

Ib wherein $R^1$, Z, Y and J are described herein, and analogs thereof are provided which are useful in treated T-cell mediated diseases. $R^2$ is defined by the following (a) heteroaryl, or heterocyclo, either of which may be optionally substituted with one to three groups $T^1$, $T^2$, $T^3$;

(b) aryl substituted with one to three groups $T^1$, $T^2$, $T^3$ provided that at least one of $T^1$, $T^2$, $T^3$ is other than H; or (c) aryl fused to a heteroaryl or heterocyclo ring wherein the combined ring system may be optionally substituted with one to three groups $T^1$, $T^2$, $T^3$.

1 Claim, No Drawings

PURINE INHIBITORS OF PHOSPHODIESTERASE (PDE) 7

This application claims priority to U.S. Provisional Application Ser. No. 60/299,287 filed Jun. 19, 2001, and U.S. Provisional Application Ser. No. 60/368,752 filed Mar. 29, 2002. The entirety of each of these applications is incorporated herein by reference.

FIELD OF THE INVENTION

The present invention relates to purine inhibitors of phosphodiesterase 7 (PDE 7) (including both selective inhibitors of PDE 7, and dual inhibitors of PDE 7 and phosphodiesterase 4 (PDE 4)), pharmaceutical compositions containing these inhibitors, and the use of these inhibitors in the treatment of leukocyte activation-associated or leukocyte-activation mediated disease and inflammatory diseases either alone or in combination with other therapeutic agents.

BACKGROUND OF THE INVENTION

Phosphodiesterases (PDEs) hydrolyze the second messenger molecules cAMP and cGMP to affect cellular signaling. At least 11 families of PDEs exist, some of which (PDE3,4,7,8) are specific for cAMP, and others (PDE5,6,9) for cGMP. Further family members (PDE1,2,10,11) have dual specificity. A recent publication demonstrated a role for PDE7 in the activation and/or proliferation of T cells(Li, Yee and Beavo, Science 283:848–851, 1999). Resting T lymphocytes express mainly PDE3 and PDE4. However, upon activation, T cells dramatically upregulate PDE7 and appear to rely on this isozyme for regulation of cAMP levels. Removal of the ability to upregulate the production of PDE7 protein by anti-sense oligonucleotides inhibited the proliferation and IL-2 production along with the maintenance of high concentrations of intracellular cAMP in CD3×CD28 stimulated T cells.

A PDE7 inhibitor is defined herein as a compound for which the $IC_{50}$ of the compound in a PDE7 inhibition assay is less than 20 micromolar (preferably less than 10 micromolar, more preferably less than 5 micromolar, most preferably less than 1 micromolar). The PDE7 $IC_{50}$ of a selective PDE7 inhibitor should be less than one-tenth the IC50 of said compound in all of the following PDE assays: PDE1, PDE3 and PDE4 (more preferably the PDE7 $IC_{50}$ of a selective PDE7 inhibitor should be less than one-twentieth the $IC_{50}$ of said compound in the following PDE assays: PDE1 and PDE3, most preferably the PDE7 $IC_{50}$ of a selective PDE7 inhibitor should be less than one-hundreth the $IC_{50}$ of said compound in a PDE3 assay).

Several isoforms of PDE1 have been identified and are distributed in heart, lung, and kidney tissue, as well as in circulating blood cells and smooth muscle cells. PDE1 inhibitors have demonstrated potent vasodilator activity. Such activity would represent an undesirable side effect in a therapeutic agent with the utilities listed in this patent for a PDE7 inhibitor. The PDE3 family of enzymes are distributed in several tissues including the heart liver, and platelets. PDE3 inhibitors have demonstrated potent cardiac iotropic activity. Such activity would represent an undesirable side effect in a therapeutic agent with the utilities listed in this patent for a PDE7 inhibitor. Several isoforms of PDE4 exist, and these are expressed in a wide variety of tissues including heart, kidney, brain, the gastrointestinal track and circulating blood cells. PDE4 inhibitors have demonstrated clinical utility for COPD, and have also been suggested to have utility for rheumatoid arthritis, and multiple sclerosis, and to possess anti-inflammatory activity. The utility of PDE4 inhibitors has been limited to some extent by their propensity to cause emesis. As such there are circumstances where it would be desirable to develop PDE7 inhibitors, which have a degree of selectivity against PDE. A selective inhibitor of PDE7 is expected to have broad application as an immunosuppressant in T cell-mediated diseases. PDE7 inhibitors will act at a different stage of the T cell signaling process compared to current immunosuppressants by inhibiting a very early stage of the T cell activation cascade. A selective inhibitor of PDE7 is also expected to have a decreased potential for clinically significant side effects compared to current immunosuppressants, therefore the primary disease indications are solid organ transplantation (SOT) and rheumatoid arthritis. Additional indications may include IBD, psoriasis, asthma and lupus.

A dual PDE7-PDE4 inhibitor (PDE4/7 or PDE7/4) is defined herein as any compound which has an IC50 in both a PDE7 and a PDE4 inhibition assay of less than 20 micromolar (preferably less than 10 micromolar, and more preferably less than 5 micromolar and most preferably less than 1 micromolar), and an IC50 in a PDE3 inhibition assay which is at least 10 times higher than the IC50 of the compound in the PDE7 assay (more preferably at least 20 times higher than the IC50 of the compound in the PDE7 assay, and most preferably at least 100 times higher than the IC50 of the compound in the PDE7 assay). A dual PDE4/7 inhibitor should have a ratio of inhibition or PDE7 IC50 divided by PDE4 IC50 of between one-tenth and 100. Inhibitors that exhibit such a ratio of inhibition include those that inhibit PDE3, PDE4 and PDE7 as described above, and further inhibit PDE1 at an IC50 at least 10 times higher than the IC50 of the compound in a PDE7 assay (more preferably at least 20 times higher than the IC50 of the compound in the PDE7 assay, and most preferably at least 100 times higher than the IC50 of the compound in the PDE7 assay). Preferred dual PDE7-PDE4 inhibitors further include those compounds that inhibit PDE3, PDE4 and PDE7 as described above, and further suppress both T cell proliferation, and TNF-alpha secretion from either THP-1 monocytes or human peripheral blood mononuclear cells at a level of less than 20 micromolar.

"Leukocyte activation" is defined herein as any or all of leukocyte (T cell, monocyte macrophage, neutrophil etc.) cell proliferation, cytokine production, adhesion protein expression, and production of inflammatory mediators. This is mediated in part by the action of PDE4 and/or PDE7 depending on the particular leukocyte under consideration.

Examples of leukocyte activation associated or leukocyte activation mediated disorders include transplant rejection, graph verses host disease, and autoimmune disorders, such as rheumatoid arthritis, multiple sclerosis, juvenile diabetes, COPD, asthma, and inflammatory bowel disease, T-cell mediated hypersensitivity diseases, ischemic or reperfusion injury, and T-cell proliferative disorders.

Dual PDE4/7 inhibitors would be expected to block the T cell component of a disease as well as possess anti-inflammatory activity. Thus a dual PDE4/7 inhibitor which is not significantly limited by emesis, may be more effective than either a selective PDE4 inhibitor or a selective PDE7 inhibitor in a variety of disease states such as rheumatoid arthritis, asthma, COPD and multiple sclerosis.

Development of either selective PDE7 inhibitors, or dual PDE7-PDE4 inhibitors will yield novel classes of therapeutics and have a novel mechanism of action by maintaining high levels of intracellular cAMP. These inhibitors would target a major unmet medical need in an area where current therapies possess significant toxicity.

Two PDE7 genes have been identified. PDE7A (EC 3.1.4.17) has two isoforms generated by alternate splicing; PDE7A1 restricted mainly to T cells and the brain, and PDE7A2 for which mRNA is expressed in a number of cell types including muscle cells. The isoforms have different sequence at the amino termini, and it is thought that this portion of each molecule is likely to be important for cellular localization of the enzyme. However, the catalytic domain of each PDE7A enzyme is identical (Han, P., Zhu, X. and Michaeli, T. Alternative splicing of the high affinity cAMP-specific phosphodiesterase (PDE7A) mRNA in human skeletal muscle and heart. *J. Biol. Chem.* 272 (26), 16152–16157 (1997)). Although abundant PDE7A2 mRNA has been identified, the presence of active enzyme in tissues is controversial, as no convincing data shows PDE7A2 protein in situ in the adult. PDE7B (EC 3.1.4.17), a second PDE7 gene family member, has approximately 70% homology to PDE7A in the enzymatic core (Sasaki, T., Kotera, J., Yuasa, K. and Omori, K. Identification of human PDE7B, a cAMP-specific phosphodiesterase *Biochem. Biophys. Res. Commun.* 271 (3), 575–583 (2000)). Two patents from Cold Spring Harbor Labs (U.S. Pat. Nos. 5,527,896 and 5,977,305) cover the methods of preparation and use of recombinant PDE7A protein. A recent publication describes moderately active PDE7 inhibitors (J. Med Chem. Vol. 43, 683 (2000)). WO 00/68230 discloses certain 1,9 dihydropurin-6-ones derivatives as PDE7 inhibitors.

SUMMARY OF THE INVENTION

The present invention provides purine compounds of the following formula (Ia) and (Ib), their enantiomers, diastereomers, tautomers and pharmaceutically acceptable salts, prodrugs and solvates thereof, for use as PDE7 inhibitors:

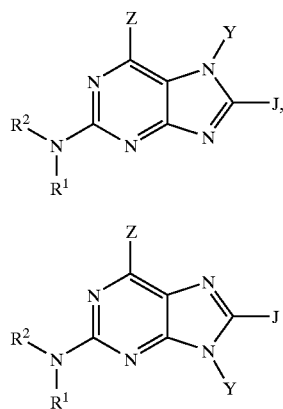

wherein:
$R^1$ is H or alkyl;
$R^2$ is
(a) heteroaryl, or heterocyclo, either of which may be optionally substituted with one to three groups $T^1$, $T^2$, $T^3$;
(b) aryl substituted with one to three groups $T^1$, $T^2$, $T^3$ provided that at least one of $T^1$, $T^2$, $T^3$ is other than H; or
(c) aryl fused to a heteroaryl or heterocyclo ring wherein the combined ring system may be optionally substituted with one to three groups $T^1$, $T^2$, $T^3$;

Y is alkyl, alkenyl, alkynyl, cycloalkyl, aryl, heterocyclo, heteroaryl, (aryl)alkyl or (heteroaryl)alkyl any of which may be optionally substituted with one to three groups $T^{1a}$, $T^{2a}$, $T^{3a}$;

J is
(a) hydrogen, halo, or —$OR^4$, or
(b) alkyl, alkenyl, alkynyl, aryl, heteroaryl, heterocyclo, or, cycloalkyl any of which may be optionally substituted with one to three groups $T^{1b}$, $T^{2b}$ $T^{3b}$;

Z is
(a) —$OR^4$, —$SR^4$, —$NR^3R^4$, —$NR^3SO_2R^{4a}$ halogen, nitro, haloalkyl; or
(b) alkyl, aryl, heteroaryl, heterocyclo, or cycloalkyl any of which may be optionally substituted with one to three groups $T^{1c}$, $T^{2c}$ $T^{3c}$;

$R^3$ is H, alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally independently substituted where valance allows with one to three groups $T^{1c}$, $T^{2c}$ $T^{3c}$;

$R^4$ is alkyl, alkenyl, aryl, (aryl)alkyl, heteroaryl, (heteroaryl)alkyl, cycloalkyl, (cycloalkyl)alkyl, heterocylo or (heterocyclo)alkyl any of which may be optionally independently substituted where valance allows with one to three groups $T^{1d}$, $T^{2d}$ or $T^{3d}$;

or $R^3$ and $R^4$ together with the nitrogen atom to which they are attached may combine to form a 4 to 8 membered heterocyclo ring optionally substituted with one to three groups $T^{1c}$, $T^{2c}$ or $T^{3c}$;

$R^{4a}$ is hydrogen, alkyl, alkenyl, aryl, heteroaryl, (aryl)alkyl, (heteroaryl)alkyl, heterocylo, (heterocyclo)alkyl, cycloalkyl or (cycloalkyl)alkyl any of which may be optionally substituted with one to three groups $T^{1d}$, $T^{2d}$ or $T^{3d}$;

$T^1$, $T^{1a}$, $T^{1b}$, $T^{1c}$, $T^{1d}$, $T^2$, $T^{2a}$, $T^{2b}$, $T^{2c}$, $T^{2d}$, $T^3$, $T^{3a}$, $T^{3b}$, $T^{3c}$ and $T^{3d}$ (hereinafter abbreviated as $T^{1-1d}$, $T^{2-2d}$, and $T^{3-3d}$) are independently (1) hydrogen or $T^6$, where $T^6$ is
(i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
(ii) (ii) a group (i) which is itself substituted by one or more of the same or different groups (i); or
(iii) (iii) a group (i) or (ii) which is independently substituted by one or more (preferably 1 to 3) of the following groups (2) to (13) of the definition of $T^{1-1d}$, $T^{2-2d}$ and $T^{3-3d}$,
(2) OH or —$OT^6$,
(3) —SH or —$ST^6$,
(4) —$C(O)_tH$, —$C(O)_tT^6$, or —O—$C(O)T^6$, where t is 1 or 2;
(5) —$SO_3H$, —$S(O)_tT^6$, or $S(O)_tN(T^9)T^6$,
(6) halo,
(7) cyano,
(8) nitro,
(9) —$T^4$—$NT^7T^8$,
(10) —$T^4$—$N(T^9)$—$T^5$—$NT^7T^8$,
(11) —$T^4$—$N(T^{10})$—$T^5$—$T^6$,
(12) —$T^4$—$N(T^{10})$—$T^5$—H,
(13) oxo, $T^4$ and $T^5$ are each independently
(1) a single bond,
(2) —$T^{11}$—$S(O)_t$—$T^{12}$—, (3) —$T^{11}$—C(O)—$T^{12}$—,
(4) —$T^{11}$—C(S)—$T^{12}$—,
(5) —$T^{11}$—O—$T^{12}$—,
(6) —$T^{11}$—S—$T^{12}$—,
(7) —$T^{11}$—O—C(O)—$T^{12}$—,
(8) —$T^{11}$—C(O)—O—$T^{12}$—,
(9) —$T^{11}$—C(=$NT^{9a}$)—$T^{12}$—, or
(10) —$T^{11}$—C(O)—C(O)—$T^{12}$—;

$T^7$, $T^8$, $T^9$, $T^{9a}$ and $T^{10}$
(1) are each independently hydrogen or a group provided in the definition of T6, or
(2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^{1-1d}$, $T^{2-2d}$ and $T^{3-3d}$, or
(3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the description of $T^{1-1d}$, $T^{2-2d}$ and $T^{3-3d}$, or
(4) $T^7$ and $T^8$ or $T^9$ and $T^{10}$ together with the nitrogen atom to which they are attached may combine to form a group —N=$CT^{13}T^{14}$ where $T^{13}$ and $T^{14}$ are each independently H or a group provided in the definition of $T^6$; and $T^{11}$ and $T^{12}$ are each independently
(1) a single bond,
(2) alkylene,
(3) alkenylene, or
(4) alkynylene.

Preferred compounds within the scope of formula I include compounds wherein $R^1$, $R^2$, Z, Y and J are selected from the following:

$R^1$ is H;

$R^2$ is
(a) heteroaryl (preferable thiazolyl) optionally substituted with $T^1$, $T^2$, $T^3$; or
(b) aryl (preferably phenyl) substituted with $T^1$ (which is other than H, preferably an electron donor group such as heteroaryl, cyano, C(O)$_t T^6$, or S(O)$_r N(T^9)$ $T^6$), and optionally substituted with $T^2$, $T^3$; or
(c) aryl fused to a heterocyclo ring (e.g., 2,3-dihydro-1H-indole bound through the aryl ring, quinolyl bound through the aryl ring (especially quinol-6-yl), quinazolinyl bound through the aryl ring (especially quinazolin-7-yl), cinnolinyl bound through the aryl ring (especially cinnolin-6-yl), isoqinolinyl bound through the aryl ring (especially isoquinol-6-yl), and phthalazinyl bound through the aryl ring (especially phthalazin-6-yl)) wherein the combined ring system may be optionally substituted with one to three groups $T^1$, $T^2$, $T^3$ (especially halo, OH, $OT^6$, alkyl, —$CO_2H$, —$CO_tT^6$, or —C(O)$NT^7T^8$);

Z is —$NR^3R^4$, —$OR^4$, —$SR^4$, or —$NHSO_2R^{4a}$;

$R^3$ is H or alkyl;

$R^4$ is (aryl)alkyl, (heteroaryl)alkyl, (heterocyclo)alkyl, cycloalkyl, heterocyclo, aryl, or alkyl any of which may be optionally substituted with $T^{1d}$, $T^{2d}$, $T^{3d}$;

or $R^3$ and $R^4$ together with the nitrogen atom to which they are attached combine to form a heterocylo group (preferably piperazinyl, morpholinyl, diazepinyl, pyrrolidinyl, or isoquinolinyl) any of which may be optionally substituted with $T^{1c}$, $T^{2c}$, $T^{3c}$;

$R^{4a}$ is alkyl, aryl optionally substituted with $T^{1d}$, $T^{2d}$, $T^{3d}$;

Y is alkyl, (aryl)alkyl or (heteroaryl)alkyl any of which may be optionally substituted with $T^{1a}$, $T^{2a}$, $T^{3a}$; and J is H.

More preferred compounds within the scope of formula I include compounds wherein $R^1$, $R^2$, Z, Y and J are selected from the following:

$R^1$ is H;

$R^2$ is
(a) thiazolyl optionally substituted with $T^1$, $T^2$, $T^3$ (preferably including alkyl, $CO_2T^6$, and C(O)$NT^7T^8$); or
(b) phenyl substituted in the para position with an electron donor group $T^1$ (including optionally substituted heteroaryl (especially substituted with alkyl), cyano, C(O)$_tT^6$, or S(O)$_rN(T^9)T^6$, more preferably $T^1$ is optionally substituted heteroaryl), and optionally further substituted with $T^2$, $T^3$;

Z is —$NR^3R^4$;

$R^3$ is H or alkyl;

$R^4$ is (aryl)alkyl, (heteroaryl)alkyl, (heterocyclo)alkyl, cycloalkyl, heterocyclo, aryl, or alkyl any of which may be optionally substituted with $T^{1d}$, $T^{2d}$, $T^{3d}$ (preferably selected from alkyl, (hydroxy)alkyl, halo, cyano, —$OT^6$, —$ST^6$, —$SO_2T^6$, —$COT^6$, —C(O)$OT^6$, —$T^4NT^7T^8$, or —$T^4N(T^{10})$—$T^5$—$T^6$ (especially where $T^4$ is a bond, —C(O)— or —$SO_2$—, and $T^5$ is —C(O)—));

or $R^3$ and $R^4$ together with the nitrogen atom to which they are attached combine to form piperazinyl, morpholinyl, diazepanyl, pyrrolidinyl, or tetrahydroisoquinolinyl, any of which may be optionally substituted with $T^{1c}$, $T^{2c}$, $T^{3c}$ (preferably selected from H, alkyl, —$OT^6$, and —C(O)$OT^6$);

Y is alkyl, (aryl)alkyl or (heteroaryl)alkyl any of which may be optionally substituted with $T^{1a}$, $T^{2a}$, $T^{3a}$ (preferably including —$SO_2T^6$); and J is H.

Preferred compounds of the present invention include compounds of formulas (IIa) and (IIb),

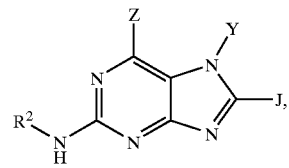

IIa

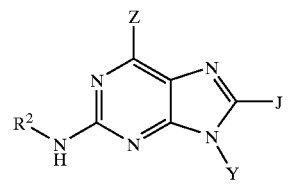

IIb wherein:

R² is chosen from:

[chemical structures]

wherein:

W is O or S, more preferably S;

X¹ is NHT⁸ or OT⁶;

X² and X²ᵃ are independently hydrogen, halo, OT⁶, alkyl, or haloalkyl;

X³ is heteroaryl (preferably, pyrimidinyl, imidazolyl, oxazolyl, or thiazolyl any of which may be further optionally substituted), cyano, C(O)$_t$T⁶, or S(O)$_t$NT⁷T⁸; and X⁴ is alkyl, haloalkyl, NHT⁸ or OT⁶.

Compounds within the scope of formula I include compounds that are dual PDE7-PDE4 inhibitors. Dual PDE7-PDE4 compounds include compounds of formulas IIIa and IIIb

[chemical structure IIIa]

[chemical structure IIIb]

wherein

R¹ is H or alkyl;

R² is optionally substituted heteroaryl, or 4-substituted aryl;

R³ is hydrogen or alkyl;

R⁴ is alkyl, optionally substituted (aryl)alkyl, optionally substituted (heteroaryl)alkyl, optionally substituted heterocylo, or optionally substituted (heterocyclo)alkyl;

or R³ and R⁴ together with the nitrogen atom to which they are attached may combine to form an optionally substituted heterocyclo ring;

Y is alkyl, optionally substituted (aryl)alkyl, or optionally substituted (heteroaryl)alkyl; and J is hydrogen or alkyl.

Preferred compounds within Formula IIIa and IIIb are those wherein

R¹ is hydrogen

R² is
  (a) thiazolyl, oxazolyl, or isoxozolyl (preferably thiazolyl) any of which may be optionally independently substituted (preferably with one or more alkyl, and/or alkoxycarbonyl groups); or
  (b) phenyl substituted at the para position with an electon-donar group T¹ (such as heteroaryl (preferably, pyrimidine, imidazolyl, oxazolyl, or thiazolyl any of which may be further optionally substituted), cyano, C(O)$_t$T⁶, or S(O)$_t$N(T⁹)T⁶) and optionally further substituted with groups T² and T³ (including cyano, C(O)$_t$T⁶, S(O)$_t$N(T⁹)T⁶, halo alkyl, and haloalkyl)

R³ is hydrogen or alkyl;

R⁴ is alkyl, optionally substituted heterocyclo, optionally substituted (aryl)alkyl (preferably substituted with a group of the formula —SO₂-alkyl), or optionally substituted (heteroaryl)alkyl;

or R³ and R⁴ together with the nitrogen atom to which they are attached may combine to form an optionally substituted heterocyclo ring; (preferably piperadinyl, piperazinyl or morpholinyl);

R⁵ is alkyl or optionally substituted (aryl)alkyl (preferably substituted with one or more alkoxy or group of the formula —SO₂-alkyl); and R⁶ is hydrogen.

More preferred compounds within Formula IIIb are those wherein:

R¹ is hydrogen.

$R^2$ is

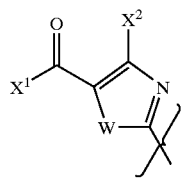

where W is O or S (preferably S), $X^1$ is alkoxy, and $X^2$ is alkyl, or 4-substituted aryl $R^3$ is hydrogen or alkyl;

$R^4$ alkyl, optionally substituted heterocyclo, optionally substituted (aryl)alkyl (preferably substituted with a group of the formula —$SO_2$-alkyl), or optionally substituted (heteroaryl)alkyl;

or $R^3$ and $R^4$ together with the nitrogen atom to which they are attached may combine to form an optionally substituted heterocyclo ring; (preferably morpholinyl);

Y is alkyl or optionally substituted (aryl)alkyl (preferably substituted with one or more alkoxy or group of the formula —$SO_2$-alkyl); and J is hydrogen.

Further preferred compounds of formula Ib are chosen such that $R^4$ or $R^5$ or both $R^4$ and $R^5$ are optionally substituted (aryl)alkyl (preferably substituted with a group of the formula —$SO_2$-alkyl, —$SO2$-$NH_2$ or 3,4-dimethoxy), or optionally substituted (heteroaryl)alkyl (preferably optionally substituted (pyridyl)alkyl);

Preferred compounds within formula III include:

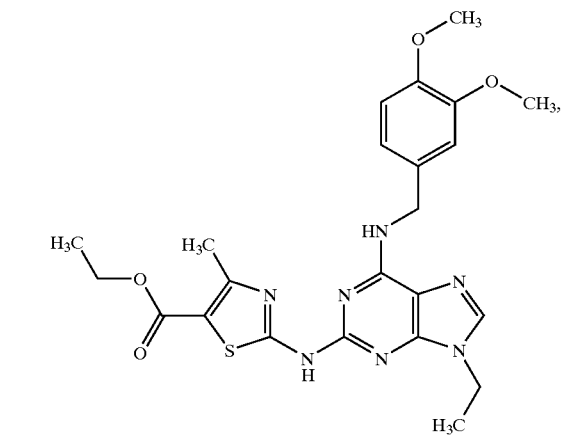

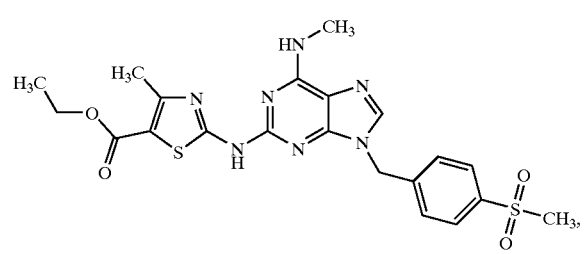

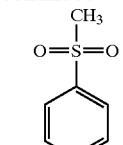

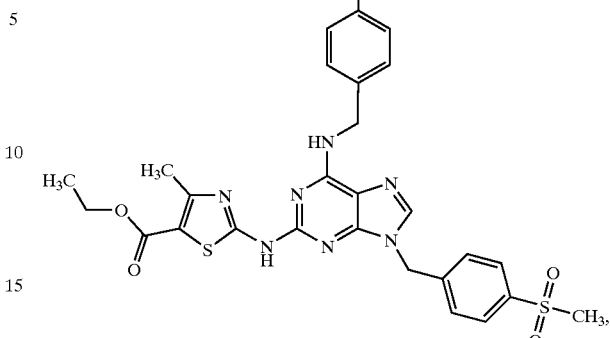

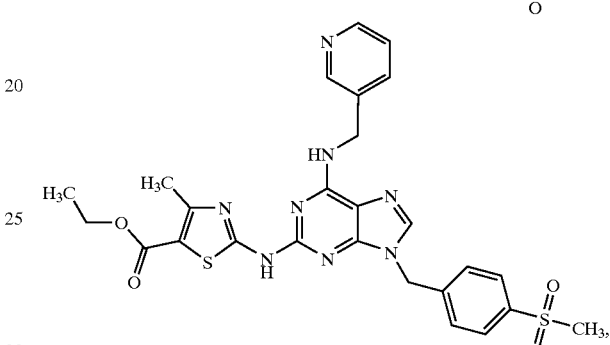

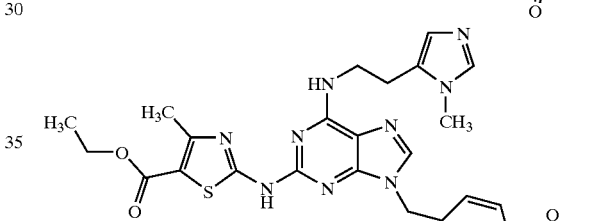

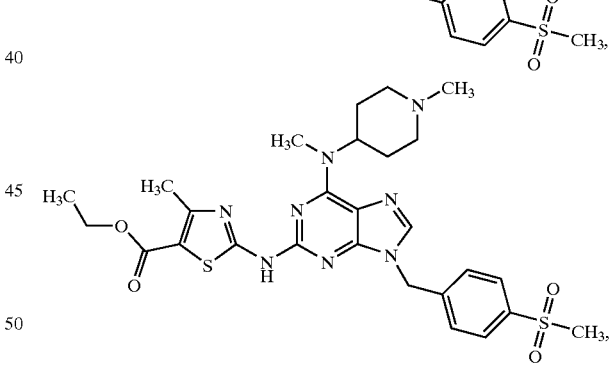

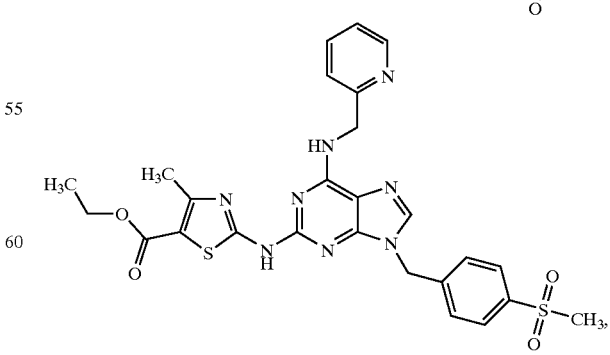

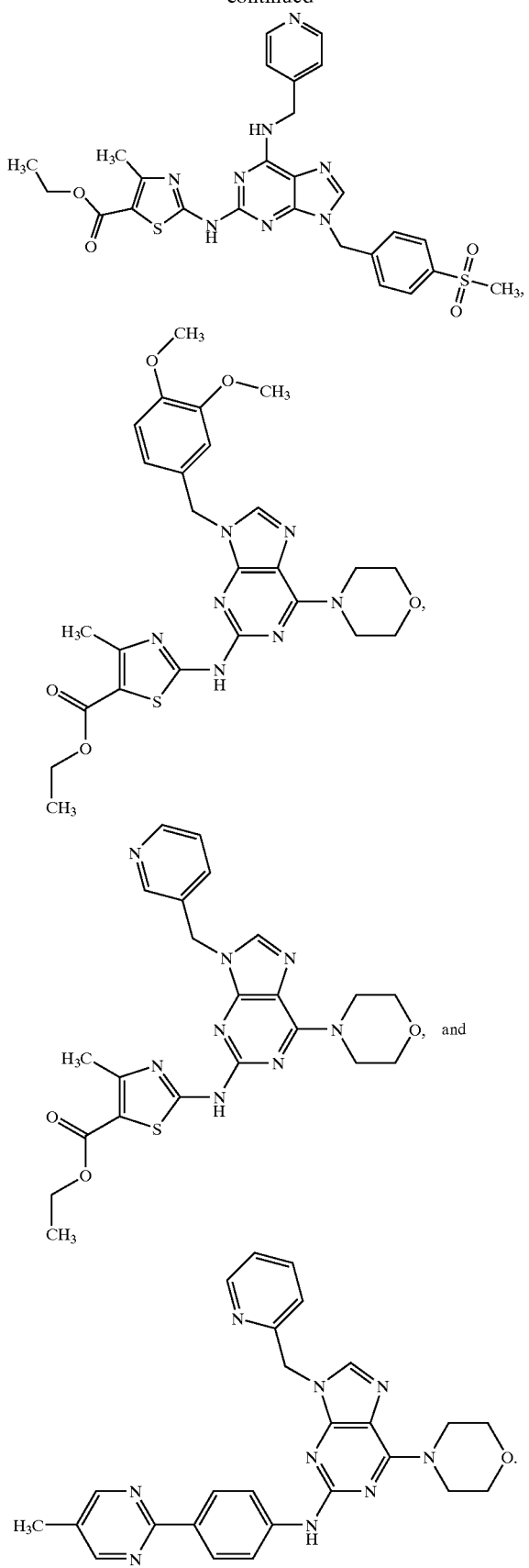

The following are definitions of the terms as used throughout this specification and claims. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred.

The term "substituted alkyl" refers to alkyl groups substituted with one or more groups listed in the definition of $T^{1-1d}$, $T^{2-2d}$, and $T^{3-3d}$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O)alkyl, and C(O)H.

The term "alkylene" refers to a straight chain bridge of 1 to 4 carbon atoms connected by single bonds (e.g., —(CH$_2$)$_x$— wherein x is 1 to 5), which may be substituted with one or more groups listed in the definition of $T^{1-1d}$, $T^{2-2d}$, and $T^{3-3d}$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl.

The term "substituted alkenyl" refers to an alkenyl group as defined above substituted with one or more groups listed in the definition of $T^{1-1d}$, $T^{2-2d}$, and $T^{3-3d}$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O)alkyl, and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above substituted with one or more groups listed in the definition of $T^{1-1d}$, $T^{2-2d}$, and $T^{3-3d}$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O)alkyl, and C(O)H.

The term "halo" refers to chloro, bromo, fluoro, and iodo.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

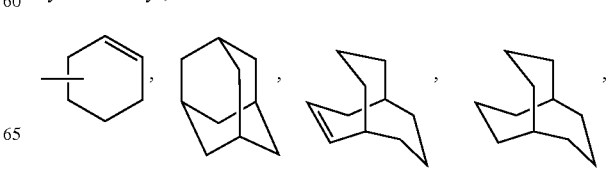

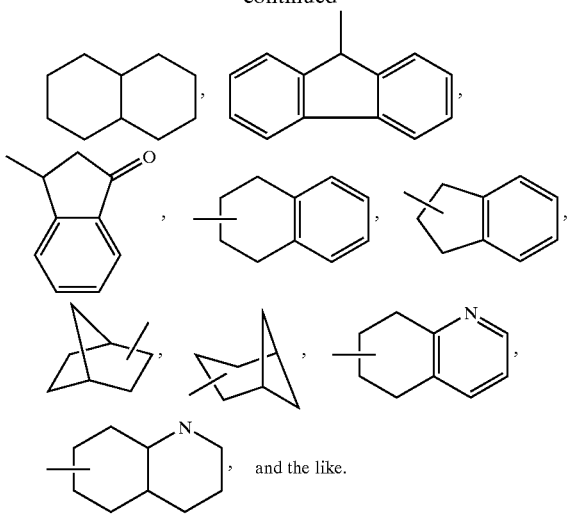

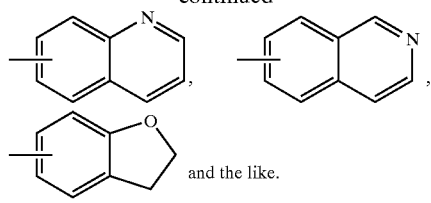

and the like.

The term "substituted cycloalkyl" refers to such cycloalkyl group as defined above substituted with one or more groups listed in the definition of $T^{1-1d}$, $T^{2-2d}$, and $T^{3-3d}$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})pO(CR_{14}R_{15})qCO_2R_7$, $CO(CR_{12}R_{13})rOR_7$, $CO(CR_{12}R_{13})pO(CR_{14}R_{15})qR_7$, $CO(CR_{12}R_{13})rNR_8R_9$, $OC(O)O(CR_{12}R_{13})mNR_8R_9$, $OC(O)N(CR_{12}R_{13})rR_7$, $O(CR_{12}R_{13})mNR_8R_9$, $NR_{10}C(O)(CR_{12}R_{13})rR_7$, $NR_{10}C(O)(CR_{12}R_{13})rOR_7$, $NR_{10}C(=NC)(CR_{12}R_{13})rR_7$, $NR_{10}CO(CR_{12}R_{13})rNR_8R_9$, $NR_{10}(CR_{12}R_{13})mOR_7$, $NR_{10}(CR_{12}R_{13})rCO_2R_7$, $NR_{10}(CR_{12}R_{13})mNR_8R_9$, $NR_{10}(CR_{12}R_{13})nSO_2(CR_{14}R_{15})qR_7$, $CONR_{10}(CR_{12}R_{13})nSO_2(CR_{14}R_{15})qR_7$, $SO_2NR_{10}(CR_{12}R_{13})nCO(CR_{14}R_{15})qR_7$, and $SO_2NR_{10}(CR_{12}R_{13})mOR_7$.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl, as well as such rings fused to a cycloalkyl, cycloalkenyl, heterocyclo, or heteroaryl ring. Examples include:

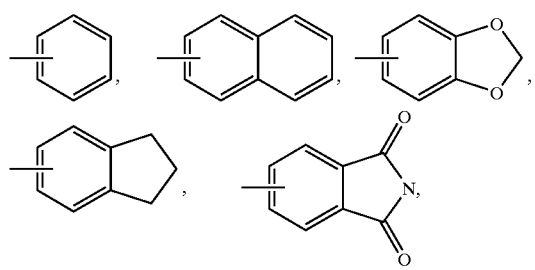

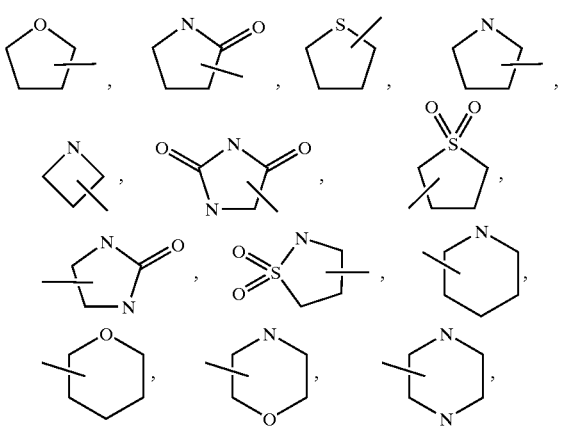

and the like.

The term "substituted aryl" refers to such aryl groups as defined above substituted with one or more groups listed in the definition of $T^{1-1d}$, $T^{2-2d}$, and $T^{3-3d}$, preferably selected from halogen, nitro, alkyl, substituted alkyl, alkenyl, cyano, cycloalkyl, substituted cycloalkyl, aryl, substituted aryl, heterocyclo, heteroaryl, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})rR_7$, $CO(CR_{12}R_{13})pO(CR_{14}R_{15})qCO_2R_7$, $CO(CR_{12}R_{13})rOR_7$, $CO(CR_{12}R_{13})pO(CR_{14}R_{15})qR_7$, $CO(CR_{12}R_{13})rNR_8R_9$, $OC(O)O(CR_{12}R_{13})mNR_8R_9$, $OC(O)N(CR_{12}R_{13})rR_7$, $O(CR_{12}R_{13})mNR_8R_9$, $NR_{10}C(O)(CR_{12}R_{13})rR_7$, $NR_{10}C(O)(CR_{12}R_{13})rOR_7$, $NR_{10}C(=NC)(CR)_{12}R_{13})rR_7$, $NR_{10}CO(CR_{12}R_{13})rNR_8R_9$, $NR_{10}(CR_{12}R_{13})mOR_7$, $NR_{10}(CR_{12}R_{13})rCO_2R_7$, $NR_{10}(CR_{12}R_{13})mNR_8R_9$, $NR_{10}(CR_{12}R_{13})nSO_2(CR_{14}R_{15})qR_7$, $CONR_{10}(CR_{12}R_{13})nSO_2(CR_{14}R_{15})qR_7$, $SO_2NR_{10}(CR_{12}R_{13})nCO(CR_{14}R_{15})qR_7$, and $SO_2NR_{10}(CR_{12}R_{13})mOR_7$ as well as pentafluorophenyl.

The terms "heterocycle", "heterocyclic", "heterocyclic group" or "heterocyclo" refer to fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

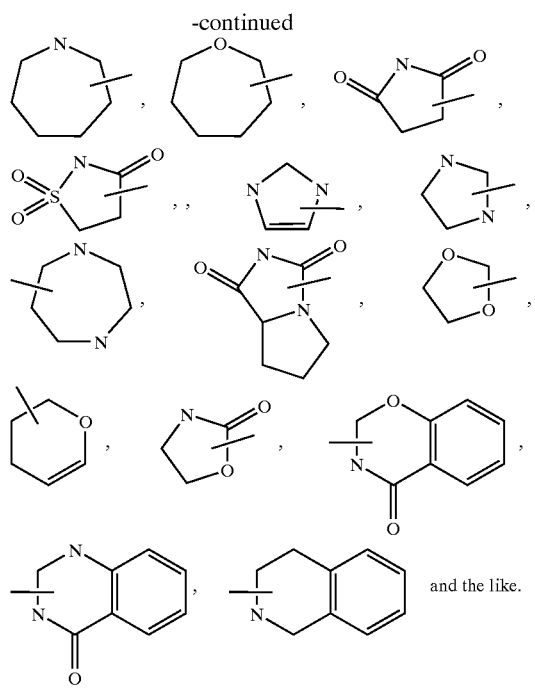

-continued and the like.

The terms "substituted heterocycle" or "substituted heterocyclo" and the like refer to such heterocylo groups as defined above substituted with one or more groups listed in the definition of $T^{1-1d}$, $T^{2-2d}$, and $T^{3-3d}$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})pO(CR_{14}R_{15})qCO_2R_7$, $CO(CR_{12}R_{13})rOR_7$, $CO(CR_{12}R_{13})pO(CR_{14}R_{15})qR_7$, $CO(CR_{12}R_{13})rNR_8R_9$, $OC(O)O(CR_{12}R_{13})mNR_8R_9$, $OC(O)N(CR_{12}R_{13})rR_7$, $O(CR_{12}R_{13})mNR_8R_9$, $NR_{10}C(O)(CR_{12}R_{13})rR_7$, $NR_{10}C(O)(CR_{12}R_{13})rOR_7$, $NR_{10}C(=NC)(CR_{12}R_{13})rR_7$, $NR_{10}CO(CR_{12}R_{13})rNR_8R_9$, $NR_{10}(CR_{12}R_{13})mOR_7$, $NR_{10}(CR_{12}R_{13})rCO_2R_7$, $NR_{10}(CR_{12}R_{13})mNR_8R_9$, $NR_{10}(CR_{12}R_{13})nSO_2(CR_{14}R_{15})qR_7$, $CONR_{10}(CR_{12}R_{13})nSO_2(CR_{14}R_{15})qR_7$, $SO_2NR_{10}(CR_{12}R_{13})nCO(CR_{14}R_{15})qR_7$, and $SO_2NR_{10}(CR_{12}R_{13})mOR_7$.

The term "heteroaryl" as used herein alone or as part of another group refers to a 5- 6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the description of $T_{1-1d}$, $T^{2-2d}$, and $T^{3-3d}$. Also an available nitrogen or sulfur atom in the heteroaryl ring can be oxidized. Examples of heteroaryl rings include

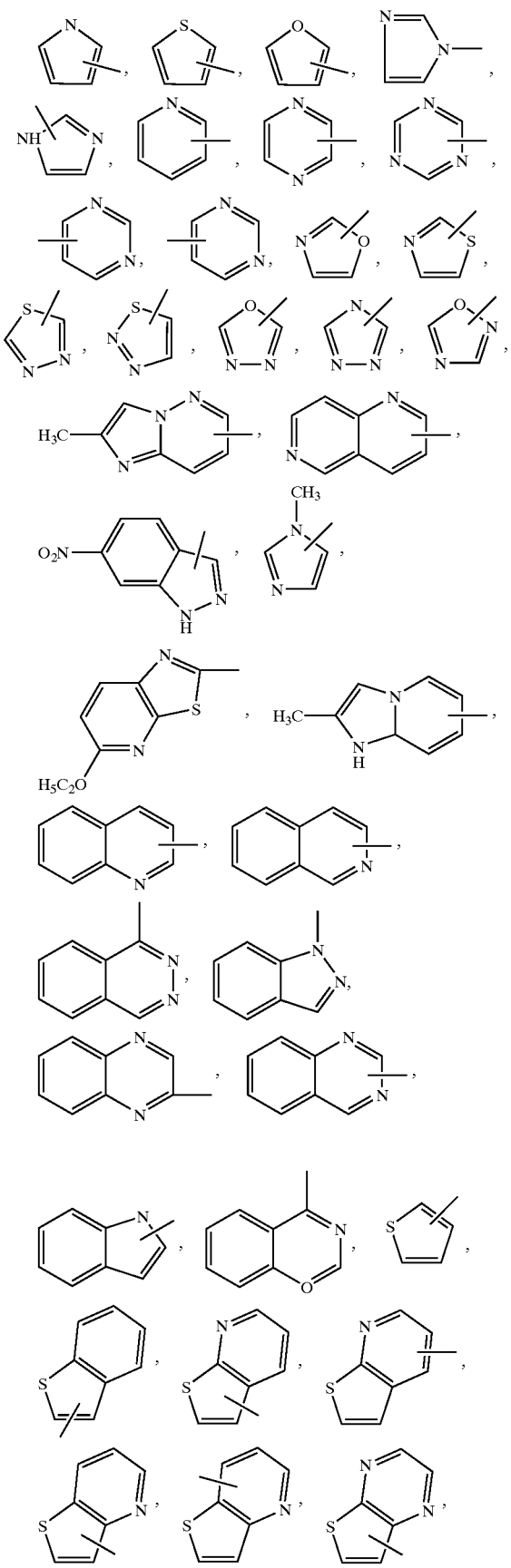

The term "substituted heteroaryl" refers to such heteroaryl groups as defined above substituted on any available atom with one or more groups listed in the definition of $T^{1-1d}$, $T^{2-2d}$, and $T^{3-3d}$, preferably selected from" refers to such heterocylo groups as defined above substituted with one or more groups listed in the definition of $T^{1-1d}$, $T^{2-2d}$, and $T^{3-3d}$, preferably selected from halogen, nitro, alkyl, substituted alkyl, alkenyl, cyano, cycloalkyl, substituted cycloalkyl, aryl, substituted aryl, heterocyclo, heteroaryl, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2N_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})pO(CR_{14}R_{15})qCO_2R_7$, $CO(CR_{12}R_{13})rOR_7$, $CO(CR_{12}R_{13})pO(CR_{14}R_{15})R_7$, $CO(CR_{12}R_{13})rNR_8R_9$, $OC(O)O(CR_{12}R_{13})mNR_8R_9$, $OC(O)N(CR_{12}R_{13})rR_7$, $O(CR_{12}R_{13})mNR_8R_9$, $NR_{10}C(O)(CR_{12}R_{13})rR_7$, $NR_{10}C(O)(CR_{12}R_{13})rOR_7$, $NR_{10}C(=NC)(CR_{12}R_{13})rR_7$, $NR_{10}CO(CR_{12}R_{13})rNR_8R_9$, $NR_{10}(CR_{12}R_{13})mOR_7$, $NR_{10}(CR_{12}R_{13})rCO_2R_7$, $NR_{10}(CR_{12}R_{13})mNR_8R_9$, $NR_{10}(CR_{12}R_{13})nSO_2(CR_{14}R_{15})qR_7$, $CONR_{10}(CR_{12}R_{13})nSO_2(CR_{14}R_{15})qR_7$, $SO_2NR_{10}(CR_{12}R_{13})nCO(CR_{14}R_{15})qR_7$, and $SO_2NR_{10}(CR_{12}R_{13})mOR_7$.

$R_7$, $R_{10}$, and $R_{11}$, are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocyclo, C(O)heteroaryl, aryl, substituted aryl, heterocyclo and heteroaryl.

$R_8$ and $R_9$ are independently selected from the group consisting of hydrogen, alkyl, substituted alkyl, cycloalkyl, substituted cycloalkyl, alkenyl, alkynyl, C(O)alkyl, C(O)substituted alkyl, C(O)cycloalkyl, C(O)substituted cycloalkyl, C(O)aryl, C(O)substituted aryl, C(O)Oalkyl, C(O)Osustituted alkyl, C(O)heterocyclo, C(O)heteroaryl, $S(O)_2$alkyl, $S(O)_2$substituted alkyl, $S(O)_2$cycloalkyl, $S(O)_2$substituted cycloalkyl, $S(O)_2$aryl, $S(O)_2$substituted aryl, $S(O)_2$heterocyclo, $S(O)_2$heteroaryl, aryl, substituted aryl, heterocyclo, and heteroaryl or $R_8$ and $R_9$ taken together with the nitrogen atom to which they are attached complete a heterocyclo or heteroaryl ring.

$R_{12}$ and $R_{14}$ are independently selected from hydrogen and alkyl or 1 to 4 carbons.

$R_{13}$ and $R_{15}$ are independently selected from hydrogen, alkyl of 1 to 4 carbons, and substituted alkyl or 1 to 4 carbons.

n is zero or an integer from 1 to 4.

m is an integer from 2 to 6.

p is an integer from 1 to 3.

q is zero or an integer from 1 to 3.

r is zero or an integer from 1 to 6.

$T^{1-1d}$, $T^{2-2d}$, and $T^{3-3d}$ are each independently (1) hydrogen or $T^6$, where $T^6$ is
  (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocylco)alkyl, heteroaryl, or (heteroaryl)alkyl;
  (ii) a group (i) which is itself substituted by one or more of the same or different groups (i); or
  (iii) a group (i) or (ii) which is independently substituted by one or more (preferably 1 to 3) of the following groups (2) to (13) of the definition of $T^{1-1d}$, $T^{2-2d}$, and $T^{3-3d}$;

(2) —OH or —$OT^6$, (3) —SH or —$ST^6$, (4) —C(O)H, —C(O)$_tT^6$, or —O—C(O)$T^6$, where t is 1 or 2;

(5) —$SO_3H$, —S(O)$_tT^6$, or S(O)$_tN(T^9)T^6$, (6) halo, (7) cyano, (8) nitro, (9) —$T^4$—$NT^7T^8$,

(10) —$T^4$—N($T^9$)—$T^5$—$NT^7T^8$,

(11) —$T^4$—N($T^{10}$)—$T^5$—$T^6$,

(12) —T⁴—N(T¹⁰)—T⁵—H,
(13) oxo,

T⁴ and T⁵ are each independently
  (1) a single bond,
  (2) —T¹¹—S(O)$_t$—T¹²—,
  (3) —T¹¹—C(O)—T¹²—,
  (4) —T¹¹—C(S)—T¹²—,
  (5) —T¹¹—O—T¹²—,
  (6) —T¹¹—S—T¹²—,
  (7) —T¹¹—O—C(O)—T¹²—,
  (8) —T¹¹—C(O)—O—T¹²—,
  (9) —T¹¹—C(=NT$^{9a}$)—T¹², or
  (10) —T¹¹—C(O)—C(O)—T¹²—

T⁷, T⁸, T⁹, T$^{9a}$ and T¹⁰
  (1) are each independently hydrogen or a group provided in the definition of T⁶, or
  (2) T⁷ and T⁸ may together be alkylene or alkenylene, completing a 3- to 8-membered saturated or unsaturated ring together with the atoms to which they are attached, which ring is unsubstituted or substituted with one or more groups listed in the description of T$^{1-1d}$, T$^{2-2d}$, and T$^{3-3d}$, or
  (3) T⁷ or T⁸, together with T⁹, may be alkylene or alkenylene completing a 3- to 8-membered saturated or unsaturated ring together with the nitrogen atoms to which they are attached, which ring is unsubstituted or substituted with one or more groups listed in the description of T$^{1-1d}$, T$^{2-2d}$, and T$^{3-3d}$, or
  (4) T⁷ and T⁸ or T⁹ and T¹⁰ together with the nitrogen atom to which they are attached may combine to form a group —N=CT¹³T¹⁴ where T¹³ and T¹⁴ are each independently H or a group provided in the definition of T⁶; and T¹¹ and T¹² are each independently
  (1) a single bond,
  (2) alkylene,
  (3) alkenylene, or
  (4) alkynylene.

"T cell-mediated diseases" refers to any disorder or disease state in which modulation of the activity of T cells is implicated in a process which results in either a pathophysiological state or a process where the normal function of T cells is intended to be suppressed for therapeutic benefit. Examples of T cell mediated disorders include transplant rejection, graph verses host disease, and autoimmune disorders, such as rheumatoid arthritis, multiple sclerosis, juvenile diabetes, asthma, and inflammatory bowel disease, T-cell mediated hypersensitivity diseases, ischemic or reperfusion injury, and T-cell proliferative disorders.

PDE7 inhibitors in accordance with the present invention are employed, typically in the form of a pharmaceutical composition including a pharmaceutically acceptable carrier for the treatment of T-cell mediated disease. The compounds employed for this purpose are typically administered in an amount from about 0.01 to 100 mg/kg/day.

The pharmaceutical compositions comprising at least one PDE7 inhibitor may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The PDE7 inhibitors may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered in the form of liposomes.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound employed in the present invention may be determined by one of ordinary skill in the art, and includes exemplary dosage amounts for an adult human of from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to inflammatory, immunological, or respiratory cell-associated disorders.

PDE7 inhibitors for use in the treatment of various T-cell mediated diseases are those covered by Formula I Compounds of Formula I include salts, prodrugs and solvates. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the Formula I, or a salt and/or solvate thereof. Solvates of the compounds of Formula I are preferably hydrates.

All stereoisomers of the present compounds, such as those which may exist due to asymmetric carbons on the R substituents of the compound of the formula I, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The compounds of Formula I are typically employed as part of a pharmaceutical composition including a pharmaceutically acceptable carrier for the treatment of respiratory and non-respiratory diseases. The compounds employed for this purpose are typically administered in an amount of from about 0.01 to 100 mg/kg/day. The compounds of Formula I are especially effective in inhibiting the PDE7 enzyme. Additionally a subset of compounds are also effective at inhibiting PDE4.

The pharmaceutical composition comprising at least one compound of Formula I may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of Formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may be based for immediate release or extended release by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer; and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to leukocyte activation or respiratory cell-associated disorders.

METHODS OF PREPARATION

Compounds of Formula I may be prepared by reference to the methods illustrated in the following Schemes A through C. As shown therein the end product is a compound having the same structural formula as Formula I. It will be understood that any compound of Formula I may be produced by Scheme A and B by the suitable selection of appropriate substitution. Schemes C shows the preparation of amides from compounds of Formula I derived from Schemes A and B. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

The methods described herein may be carried out with starting materials and/or reagents in solution or alternatively, where appropriate, with one or more starting materials or reagents bound to a solid support (see (1) Thompson, L. A., Ellman, J. A., *Chemical Reviews,* 96, 555–600 (1996); (2) Terrett, N. K., Gardner, M., Gordon, D. W., Kobylecki, R. J., Steele, J., *Tetrahedron,* 51, 8135–8173 (1995); (3) Gallop, M. A., Barrett, R. W., Dower, W. J., Fodor, S. P. A., Gordon, E. M., *Journal of Medicinal Chemistry,* 37, 1233–1251 (1994); (4) Gordon, E. M., Barrett, R. W., Dower, W. J., Fodor, S. P. A., Gallop, M. A., *Journal of Medicinal Chemistry,* 37, 1385–1401 (1994); (5) Balkenhohl, F., von dem Bussche-Hünnefeld, Lansky, A., Zechel, C., *Angewandte Chemie International Edition in English,* 35, 2288–2337 (1996); (6) Balkenhohl, F., von dem Bussche-Hünnefeld, Lansky, A., Zechel, C., *Angewandte Chemie,* 108, 2436–2487 (1996); Gray N. S.; Kwon, S.; Schultz, P. G.; Tetrahedron Lett 38, 1161–1164 (1997), Nugiel, D. A.; Cornelius, L. A. M.; Corbett, J. W.; J Org Chem 62, 201–203 (1997), Norman, T. C.; Gray, N. S.; Koh, J. T.; Schultz, P. G.; J Am Chem Soc, 118, 7430–7431. (1996), and (7) Sofia, M. J., *Drugs Discovery Today,* 1, 27–34 (1996)).

Scheme A illustrates a general method for the solid phase preparation of compounds of Formula Ia or Ib. Solid supports enable a molecule of interest to be synthesized with facile removal of reagents and is used by one skilled in the art as an alternative to the conventional synthesis of compounds in solution. A starting Compound I anchored to a suitable resin (such as a SASRIN resin, as indicated by the darkened sphere) can be treated with a reducing agent such as sodium cyanoborohydride in the presence of an amine II to give an amine III. Coupling with a appropriate dichloroheterocyle, in this case a dichloropurine, derivative IV in the presence of a base such as diisopropyl ethyl amine in a solvent such as N-methyl pyrrolidone gives substituted purine V. Conversion of V under palladium-catalyzed coupling conditions in the presence of an amine VI gives the resin anchored Compound VII. Cleavage from the resin using acidic conditions such as TFA gives compound VIII which are examples of compounds of Formula Ia.

Scheme A

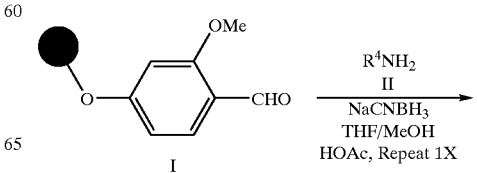

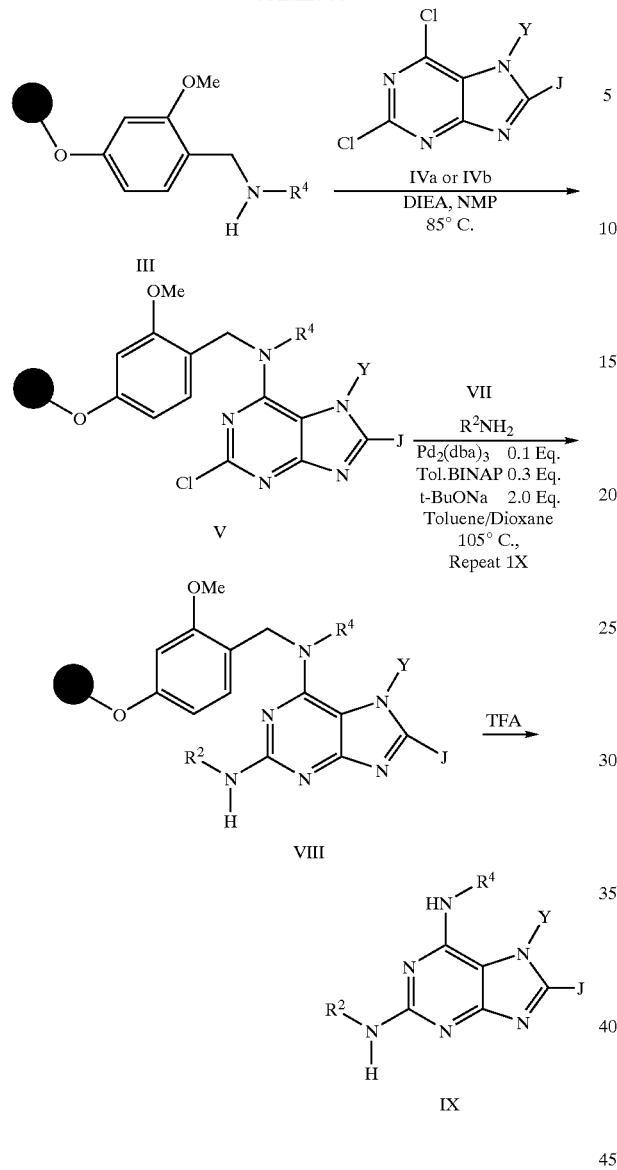

Scheme B1 outlines the solution phase synthesis of compounds of Formula Ia and Ib. Compound X is treated with a Y-halide in the presence of a base such as potassium carbonate in acetone to give a mixture of Compounds IVa and IVb. Separation of the isomers is accomplished using standard chromatography techniques. The intermediate IVa or IVb may be reacted with reagent XI, which may be an or an amine, alcohol, a thiol or a sulfonamide on the presence of a suitable base to provide intermediate XII. Conversion of XII under palladium-catalysed coupling conditions in the presence of an amine XIII gives compound IX.

Scheme C outlines the conversion of esters of Formula 1a to amides of Formula Ia. Hydrolysis of the ester of Compound IXa under basic conditions such as sodium hydroxide affords the acid XIIIa. Coupling of XIIIa under standard amide bond coupling techniques (EDC/HOAt) with the appropriate amine XIV gives the desired amide XVa.

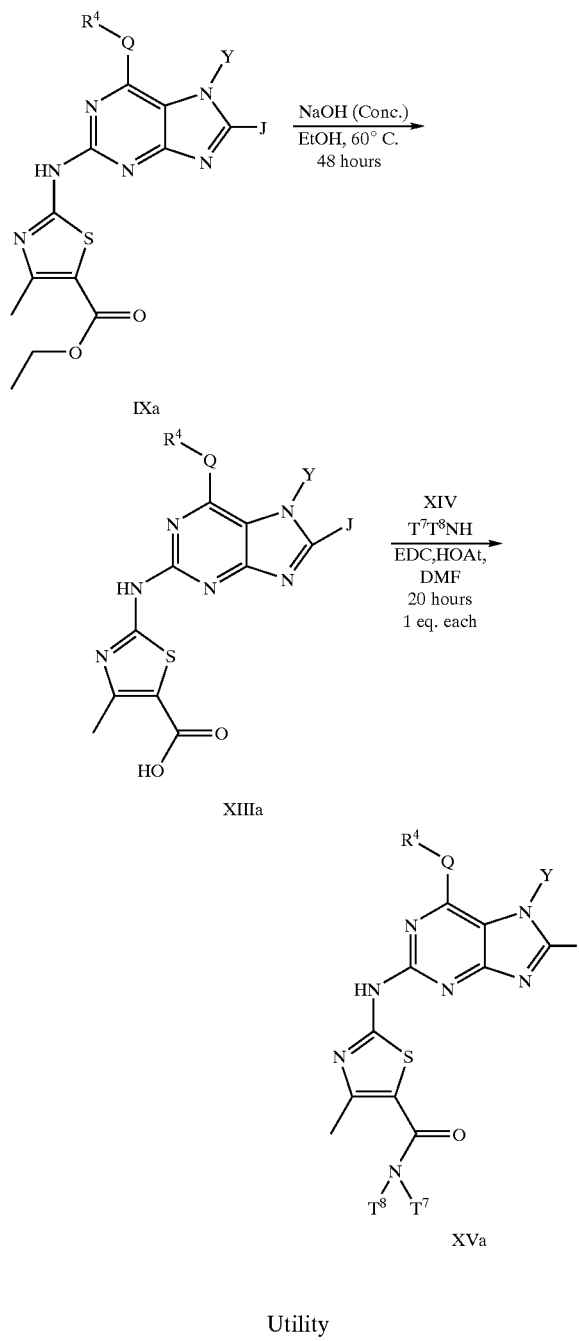

Scheme C

IXa

XIIIa

XVa

Utility

Selective PDE7 inhibitors or dual PDE7-PDE4 inhibitors including compounds of formulas I, are useful in the treatment (including prevention, partial alleviation or cure) of leukocyte activation-associated disorders, which include (but are not limited to) disorders such as: transplant rejection (such as organ transplant, acute transplant, xenotransplant or heterograft or homograft such as is employed in burn treatment); protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (e.g., asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The term "leukocyte activation-associated disorder" or "leukocyte activation-mediated disorder" as used herein includes each of the above referenced diseases or disorders. The compounds of the present invention are useful for treating the aforementioned exemplary disorders irrespective of their etiology.

Those present compounds which are dual PDE7/4 inhibitors may be more effective than either a selective PDE4 inhibitor or a selective PDE7 inhibitor in the above mentioned disease states, as a result of either additive or synergistic activity resulting from the combined inhibition of PDE7 and PDE4.

The present invention thus provides methods for the treatment of disorders as discussed above comprising the step of administering to a subject in need thereof of at least one selective PDE7 inhibitor or at least one dual PDE7-PDE4 inhibitor for the treatment of leukocyte activation-associated or leukocyte-activation mediated disease. Other therapeutic agents such as those described below may be employed with the compounds of the present invention. In the methods of the present invention, such other therapeutic agent(s) may be administered prior to, simultaneously with or following the administration of the compound(s) of the present invention.

The methods of treating diseases which would benefit from the inhibition of PDE7 or the inhibition of both PDE7-PDE4 by a dual agent may comprise administering compounds of Formula (I) alone or in combination with each other and/or other suitable therapeutic agents useful in treating such conditions such as: immunosuppressants such as, cyclosporins (e.g., cyclosporin A), anti-IL-1 agents, such as Anakinra, the IL-1 receptor antagonist, CTLA4-Ig, antibodies such as anti-ICAM-3, anti-IL-2 receptor (Anti-Tac), anti-CD45RB, anti-CD2, anti-CD3, anti-CD4, anti-CD80, anti-CD86, monoclonal antibody OKT3. agents blocking the interaction between CD40 and CD154, such as antibodies specific for CD40 and/or CD154 (i.e., CD40L), fusion proteins constructed from CD40 and CD154 (CD40Ig and CD8-CD154), interferon beta, interferon gamma, methotrexate, FK506 (tacrolimus, Prograf), rapamycin (sirolimus or Rapamune)mycophenolate mofetil, leflunomide (Arava), azathioprine and cyclophosphamide, inhibitors, such as nuclear translocation inhibitors, of NF-kappa B function, such as deoxyspergualin (DSG), non-steroidal antiinflammatory drugs (NSAIDs) such as ibuprofen, cyclooxygenase-2 (COX-2) inhibitors such as celecoxib (Celebrex) and rofecoxib (Vioxx), or derivatives thereof, steroids such as prednisone or dexamethasone, gold compounds TNF-α inhibitors such as tenidap, anti-TNF antibodies or soluble TNF receptor such as etanercept (Enbrel), inhibitors of p-38 kinase such as BIRB-796, RO-3201195, VX-850, and VX-750, beta-2 agonists such as albuterol, levalbuterol (Xopenex), and saltmeterol (Screvent), inhibitors of leukotriene synthesis such as montelukast (Singulair) and zariflukast (Accolate), and anticholinergic agents such as ipratropium bromide (Atrovent). PDE4 inhibitors such as Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490, PDE7 inhibitors such as IC242, (Lee, et. al. PDE7A is expressed in human B-lymphocytes and is up-regulated by elevation of intracellular cAMP. *Cell Signalling,* 14, 277–284, (2002)) and also include compounds disclosed in the following patent documents: WO 0068230, WO 0129049, WO 0132618, WO 0134601, WO 0136425, WO 0174786, WO 0198274, WO 0228847, U.S. Provisional Application Serial No. 60/287,964, and U.S. Provisional Application Serial No. 60/355,141 anti-cytokines such as anti-IL-1 mAb or IL-1 receptor agonist, anti-IL-4 or IL-4 receptor fusion proteins and PTK inhibitors such as those disclosed in the following U.S. Patents and Applications, incorporated herein by reference in their entirety: U.S. Pat. Nos. 6,235,740, 6,239,133, U.S. application Ser. No. 60/065,042, filed Nov. 10, 1997, U.S. application Ser. No. 09/173,413, filed Oct. 15, 1998, and U.S. Pat. No. 5,990,109.

See the following documents and references cited therein: Hollenbaugh, D., Douthwright, J., McDonald, V., and Aruffo, A., "Cleavable CD40Ig fusion proteins and the binding to sgp39", *J. Immunol. Methods* (Netherlands), 188(1), p. 1–7 (Dec. 15, 1995); Hollenbaugh, D., Grosmaire, L. S., Kullas, C. D., Chalupny, N. J., Braesch-Andersen, S., Noelle, R. J., Stamenkovic, I., Ledbetter, J. A., and Aruffo, A., "The human T cell antigen gp39, a member of the TNF gene family, is a ligand for the CD40 receptor: expression of a soluble form of gp39 with B cell co-stimulatory activity", *EMBO J* (England), 11(12), p 4313–4321 (December 1992); and Moreland, L. W. et al., "Treatment of rheumatoid arthritis with a recombinant human tumor necrosis factor receptor (p75)-Fc fusion protein, *New England J. of Medicine,* 337(3), p. 141–147 (1997).

Compounds present invention (especially selective PDE 7 inhibitors) may also be employed in combination with PDE 4 inhibitors. Examples of selective PDE4 inhibitors currently in development, which can be used in combination with compounds of the present invention include Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490.

The above other therapeutic agents, when employed in combination with the compounds of the present invention, may be used, for example, in those amounts indicated in the Physicians' Desk Reference (PDR) or as otherwise determined by one of ordinary skill in the art.

Use of the compounds of the present invention as encompassed by formula I in treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The combined activity of the present compounds towards T-cells and other PDE7-expressing cells may be of value in the treatment of any of the aforementioned disorders. Additionally those present compounds which are dual PDE4/7 inhibitors may be more effective than either a selective PDE4 inhibitor or a selective PDE7 inhibitor in the above mentioned disease states.

In a particular embodiment, the compounds of the present invention are useful for the treatment of the aforementioned exemplary disorders irrespective of their etiology, for example, for the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, respiratory diseases such as asthma, COPD and bronchitis or atopic dermatitis whether or not associated with leukocyte activation.

PDE-containing Cell Lysates

Hut78 cells were grown in 10% FCS in Iscoves Modified Dulbecco's Medium (Gibco BRL-Life Technologies, Grand Island, N.Y.) with antibiotics. Cells were centrifuged and resuspended in four volumes of [40 mM Tris (pH 7.5)/50 μM EDTA/200 uM PMSF with a cocktail of Protease inhibitors (Boehringher Mannheim, Indianapolis, Ind.)] at 4 C. Cells were homogenized using a Virtis homogenizer, and the lysate was centrifuged twice for 15 min at 15,000×g. Glycerol was added to a final volume of 50% for storage at −20 C.

SPA Assay

Inhibition of PDE activity in Hut78 cell lysate was determined using an SPA specific for cAMP (Amersham Pharmacia Biotech, Buckinghamshire, UK) according to the manufacturers instructions with minor modifications. Enzyme assays were performed at room temperature in the presence of 50 mM Tris HCl, pH7.5, containing 8.3 mM $MgCl_2$, 1.7 mM EGTA and 0.5 mg/mL BSA. Each assay was performed in a 100 µL reaction volume in 96 well microtitre plates containing the above buffer, 0.3 ul of Hut78 cell lysate treated with 2 uM Zardaverine to inhibit PDE3 and PDE4, 0.05 uCi of [5',8-$_3$H] Adenosine 3',5'-cyclic phosphate as an ammonium salt for 20 min. The reaction was terminated by the addition of 50 µl PDE SPA beads (1 mg) water with 10 mM cold cAMP (Sigma, St. Louis Mo.). The reaction mix was allowed to settle for 20 minutes before counting in a Top Count-NXT scintillation counter (Packard BioScience, Meriden, Conn.). For individual PDE enzymes other than PDE7, the assay was essentially unchanged except that $^3$H-cyclic GMP was used as the substrate for PDE1, PDE5 and PDE6. The following PDEs/activators and enzyme sources were used: PDE1, bovine (Sigma St Louis), calmodulin; PDE2, rat kidney, cGMP; PDE3, human platelet; PDE4, rat kidney; PDE5, human platelet, and PDE6, bovine retina.

T Cell Proliferation Assay

Peripheral blood mononuclear cells (PBMC) were isolated from whole blood by density gradient centrifugation over Lymphoprep, 1.077. Cells were plated into 96 well U-bottom plates at 2.5×10$_5$ cells/well in 10% FBS RPM1 1640 (Life Technologies/Gibco-BRL) containing 10 ug/ml anti-CD3 (G19-4, Bristol-Myers Squibb P.R.I., Princeton, N.J.) and 1 ug/ml anti-CD28 (9.3, Bristol-Myers Squibb P.R.I.) in the presence and absence of inhibitors. DMSO (used as a solvent for inhibitors) was added to the medium at 0.1% final concentration. The total volume per well was 200 µL. Cells were incubated at 37 C 5% CO2 for 3 days, at which time 0.5 µCi of $^3$H-thymidine was added to each well. Six hours following the addition of $^3$H-thmidine, the plates were harvested onto filter plates, 30 ul EcoLite scintillant (ICN, Costa Mesa, Calif.) was added per well, and plates read on a Top Count-NXT scintillation counter.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI1640 supplemented with 10% FBS and DMSO at a final concentration of 0.2%. Cells (2×10$^5$/well in U-bottom 96 well plates) were pre-incubated with compounds for 30 min at 37 C prior to addition of lipopolysaccharide (LPS) at a final concentration of 6.25 ng/ml in a total volume of 200 µL. After 4 h at 37 C, 50 µL of supernatant was carefully aspirated for detection of soluble TNFα. Soluble TNFα was detected by ELISA developed by R&D Systems (Minneapolis, Minn.) according to the manufacturers instructions.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| Abbreviations | |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc | tert-butoxycarbonyl |
| DIC | 1,3-Diisopropyl carbodiimide |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disulfide |
| LC | liquid chromatography |
| Me | Methyl |
| MeOH | Methanol |
| min. | Minutes |
| M$^+$ | (M + H)$^+$ |
| M$^{+1}$ | (M + H)$^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat. | Saturated |
| S-Tol-BINAP | (S)-(−)-2,2'-Bis(di-p-tolylphosphino)-1,1'-binapthyl |
| TFA | Trifluoroacetic acid |
| THF | Tetrahydrofuran |
| YMC | YMC Inc, Wilmington, NC 28403 |

Unless otherwise noted HPLC conditions used to determine retention times; 2 min gradient 0–100% B in A(A; 0.1% TFA in 90/10 water/methanol; B; 0.1% TFA in 10/90 water/methanol) using a YMC turbopack column at 220 nm.

Preparation of N-7-ethyl-2,6-dichloropurine and N-9-ethyl-2,6-dichloropurine

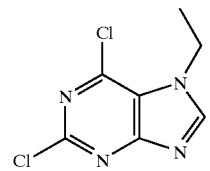

2,6-Dichloropurine (5.0 g, 26.7 mmol), potassium carbonate (11.1 g, 80 mmol) and, ethyl iodide (6.4 ml, 80 mmol) were refluxed in acetone (250 ml) for 2–3 h until tlc (30% ethyl acetate in dichloromethane) showed no more starting material. The mixture was cooled, filtered and concentrated to give a 3:1 mixture of N-9:N-7 alkylated purine as determined by HPLC. The products were purified by chromatography over silica gel (5% ethyl acetate in dichloromethane→40% ethyl acetate in dichloromethane) to give N-9-ethyl-2,6-dichloropurine (3.71 g, 64.2% yield) and N-7-ethyl-2,6-dichloropurine (0.943 g, 16.3% yield).

Example A1–A29

A1.1: A General Method for the Preparation of Purines via Solid Phase Techniques

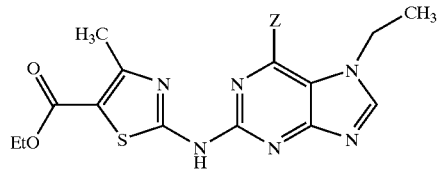

A mixture of SASRIN aldehyde resin (10 g, 10.7 mmol), the amine (21.4 mmol) and THF (67 ml) in 500 ml round-bottom flask was evacuated and purged three times with nitrogen. A solution of zinc chloride (0.5 M in THF, 43 ml, 21.4 mmol) was added and the resin was vortexed for 2–3h. Borane-pyridine complex (900 µl, 9 mmol) was added dropwise and the mixture was vortexed for 16 h with occasional release of gas. The resin was filtered and successively washed with THF:water:AcOH 18:2:1, water, THF, methanol, dichloromethane and the resin was dried under reduced pressure.

The loading of the resin was determined by benzoylating a portion of the resin. To a suspension of the resin (100 mg, ~0.09 mmol), N,N-diisopropyl-N-ethylamine (100 µl, 0.56 mmol), and a crystal of 4-(N,N-dimethylamino)pyridine in dichloromethane was added benzoyl chloride and the mixture was vortexed for 2 h. The resin was washed with many fractions of dichloromethane and the resin was cleaved with a mixture of THF:dichloromethane (1 ml each) for 1 h. The resin was filtrated and the solvent were concentrated to give the benzoylated amine.

A suspension of the resin in NMP (10 ml/g of resin), Compound 1 (1.5 eq.) and N,N-diisopropyl-N-ethylamine (5 eq.) were purged with nitrogen and vortexed at 85° C. for 16 h. The resins were filtered, washed with NMP, THF, dichloromethane and they were dried under vacuum. The loading was evaluated by cleaving an aliquot of the resin with a mixture of TFA:dichloromethane (2 ml, 1:1) for ~2 h. The yield is obtained after concentration of the supernatant.

The chloropurine resins (100 mg~0.08 mmol) were distributed into 2 drams (8 ml), TEFLON-lined capped vials. The nucleophiles, in this example, ethyl 2-amino-4-methylthiazole-5-carboxylate, were added and the vials were evacuated and then purged with nitrogen. A stock solution of consisting of $Pd_2(dba)_3$ (320 mg, ~0.008 mmol/500 µl), (+)-TolBINAP (640 mg, 0.024 mmol/500 µl), tBuONa (600 mg, 0.16 mmol/500 µl) and styrene (600 µl, 0.16 mmol/500 µl) in dioxane (20 ml) was prepared under nitrogen and an aliquot (500 µl) was added to each vials. Toluene (300 µl) was added to each vials and nitrogen was bubbled through each solutions for ~1 min. The vials were closed and heated to 110° C. for ~16 h. The vials were cooled and the supernatant solution were carefully decanted from each resin under nitrogen. The resin were then washed with anhydrous dioxane (3 ml) and the resin were treated again with the nucleophiles and the catalyst mixture as described previously. The solvents were drained and the resins were washed with THF:water (1:1), THF:water:acetic acid (5:2:0.01), THF, dichloromethane, methanol, dichloromethane, methanol and dichloromethane. The compounds were released from the resin by treatment with TFA in dichloromethane (2 ml, 1:1) for 30–45 min. The resin was filtered and the solvent were concentrated. The products were either tested directly or purified by reverse-phase chromatography.

A1.2 A General Method for the Preparation of Purines in Solution

A1.2a: General Method for Preparation of-6-Substituted Purines in Solution

To a solution of N-7-ethyl-2,6-dichloropurine (116 mg, 0.53 mmol) in n-butanol (2ml) was added the appropriate nucleophile, in this example an amine, (0.56 mmol, 1.05 eq) and diisopropylethylamine (69 mg, 1.76 mmol, 3.3 eq.). The solution mixture was stirred and heated at 100° C. for 8 hours. The solution was cooled and the white precipitate formed was filtered and washed with methanol. The intermediate monochloride, A1.2a, (0.44 mmol, 83%) was dried by vacuum and use as is in the next reaction. LC/MS is taken and confirmed the structure (m/z 348, M+H⁺). The filtrate can be chromatographed by Prep HPLC to yield more of the product.

A1.2b: General Method for Preparation of-2-Substituted Purines in Solution

To a 2 dram vial was added the intermediate monochloride, A1.2a, (0.44 mmol), the appropriate amine (0.89 mmol, 2.0 eq.), in this example, ethyl 2-amino-4-methylthiazole-5-carboxylate, palladium catalyst, in most cases either tris(dibenzylidineacetone)dipalladium (0) or palladium acetate (0.04 mmol, 0.1 eq), S-Tol-BINAP (90.2 mg, 0.13 mmol, 0.3 eq.), sodium tert-butoxide (85.1 mg, 0.89 mmol, 2.0 eq), toluene (1.5 ml) and dioxane (1.5 ml). The solution mixture was heated to 105° C. for 18 h. The solution was filter through florisil and concentrated in vacuo. The crude product mixture was purified by Prep HPLC. The product was isolated by concentrating the TFA solution and checked by LC/MS.

Shown below are examples prepared by the above methods.

TABLE A

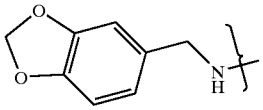

| Ex# | Z | Name | HPLC Retention | MS Reported |
|---|---|---|---|---|
| A1 | 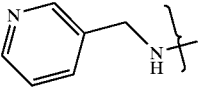 | 2-[[6-[(1,3-Benzodioxol-5-ylmethyl)amino]-7-ethyl-7H-purin-2-yl]amino]-4-methyl-5-thiazolecarboxylic acid ethyl ester | 1.59 | 482.05 |
| A2 | 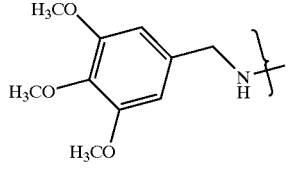 | 2-[[7-Ethyl-6-[(3-pyridinylmethyl)amino]-7H-purin-2-yl]amino]-4-methyl-5-thiazolecarboxylic acid ethyl ester | 1.24 | 439.15 |
| A3 | 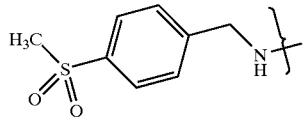 | 2-[[7-Ethyl-6-[[(3,4,5-trimethoxyphenyl)methyl]amino]-7H-purin-2-yl]amino]-4-methyl-5-thiazolecarboxylic acid ethyl ester | 1.55 | 528.11 |
| A4 | 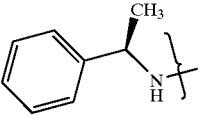 | 2-[[7-Ethyl-6-[[[4-(methylsulfonyl)phenyl]methyl]amino]-7H-purin-2-yl]amino]-4-methyl-5-thiazolecarboxylic acid ethyl ester | 1.36 | 516.05 |
| A5 | 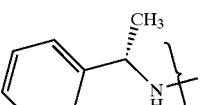 | 4-Methyl-2-[[6-[[(1R)-1-phenylethyl]amino]-7-ethyl-7H-purin-2-yl]amino]-5-thiazolecarboxylic acid ethyl ester | 1.62 | 452.07 |
| A6 | 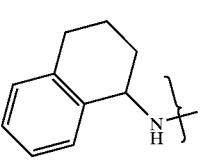 | 4-Methyl-2-[[6-[[(1S)-1-phenylethyl]amino]-7-ethyl-7H-purin-2-yl]amino]-5-thiazolecarboxylic acid ethyl ester | 1.69 | 452.06 |
| A7 | 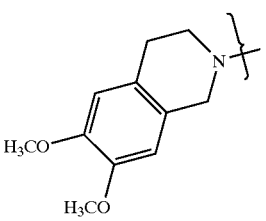 | 2-[[7-Ethyl-6-[(1,2,3,4-tetrahydro-1-naphthalenyl)amino]-7H-purin-2-yl]amino]-4-methyl-5-thiazolecarboxylic acid ethyl ester | 1.63 | 478.59 |
| A8 | 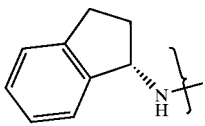 | 2-[[7-Ethyl-6-(1,2,3,4-tetrahydro-6,7-dimethoxy-2-isoquinolinyl)-7H-purin-2-yl]amino]-4-methyl-5-thiazolecarboxylic acid ethyl ester | 1.62 | 525.72 |
| A9 |  | 2-[[6-[[(1R)-2,3-Dihydro-1H-inden-1-yl]amino]-7-ethyl-7H-purin-2-yl]amino]-4-methyl-5-thiazolecarboxylic acid ethyl ester | 1.68 | 464.31 |

TABLE A-continued

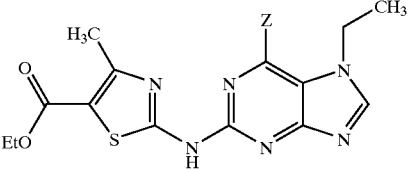

| Ex# | Z | Name | HPLC Retention | MS Reported |
|---|---|---|---|---|
| A10 | 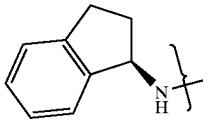 | 2-[[6-[[(1S)-2,3-Dihydro-1H-inden-1-yl]amino]-7-ethyl-7H-purin-2-yl]amino]-4-methyl-5-thiazolecarboxylic acid ethyl ester | 1.67 | 464.51 |
| A11 | 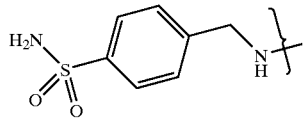 | 2-[[6-[[[4-(Aminosulfonyl)phenyl]methyl]amino]-7-ethyl-7H-purin-2-yl]amino]-4-methyl-5-thiazolecarboxylic acid ethyl ester | 1.41 | 517.00 |
| A12 | 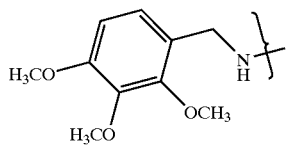 | 2-[[7-Ethyl-6-[[(2,3,4-trimethoxyphenyl)methyl]amino]-7H-purin-2-yl]amino]-4-methyl-5-thiazolecarboxylic acid ethyl ester | 1.58 | 528.15 |
| A13 | 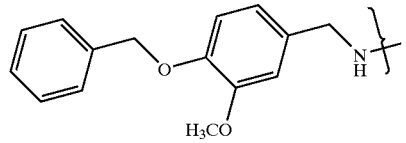 | 2-[[7-Ethyl-6-[[[3-methoxy-4-(phenylmethoxy)phenyl]methyl]amino]-7H-purin-2-yl]amino]-4-methyl-5-thiazolecarboxylic acid ethyl ester | 1.62 | 574.15 |
| A14 | 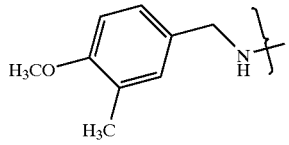 | 2-[[7-Ethyl-6-[[(4-methoxy-3-methylphenyl)methyl]amino]-7H-purin-2-yl]amino]-4-methyl-5-thiazolecarboxylic acid ethyl ester | 1.67 | 482.15 |
| A15 | 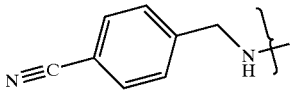 | 2-[[6-[[(4-Cyanophenyl)methyl]amino]-7-ethyl-7H-purin-2-yl]amino]-4-methyl-5-thiazolecarboxylic acid ethyl ester | 1.46 | 463.14 |
| A16 | 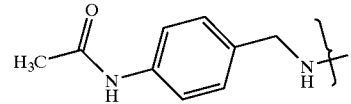 | 2-[[6-[[[4-(Acetylamino)phenyl]methyl]amino]-7-ethyl-7H-purin-2-yl]amino]-4-methyl-5-thiazolecarboxylic acid ethyl ester | 1.39 | 495.13 |
| A17 | 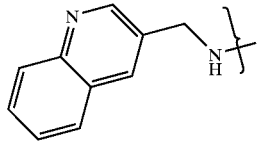 | 2-[[7-Ethyl-6-[(3-quinolinylmethyl)amino]-7H-purin-2-yl]amino]-4-methyl-5-thiazolecarboxylic acid ethyl ester | 1.31 | 489.13 |
| A18 | 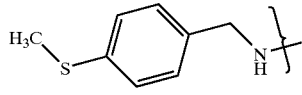 | 2-[[7-Ethyl-6-[[[4-(methylthio)phenyl]methyl]amino]-7H-purin-2-yl]amino]-4-methyl-5-thiazolecarboxylic acid ethyl ester | 1.68 | 484.08 |

TABLE A-continued

| Ex# | Z | Name | HPLC Retention | MS Reported |
|---|---|---|---|---|
| A19 | | 2-[[7-Ethyl-6-[[[4-(methoxycarbonyl)phenyl]methyl]amino]-7H-purin-2-yl]amino]-4-methyl-5-thiazolecarboxylic acid ethyl ester | 1.54 | 496.10 |
| A20 | | 2-[[7-Ethyl-6-[[(7-methoxy-1,3-benzodioxol-5-yl)methyl]amino]-7H-purin-2-yl]amino]-4-methyl-5-thiazolecarboxylic acid ethyl ester | 1.61 | 512.12 |
| A21 | | 2-[[6-[(1,3-Benzodioxol-4-ylmethyl)amino]-7-ethyl-7H-purin-2-yl]amino]-4-methyl-5-thiazolecarboxylic acid ethyl ester | 1.61 | 482.13 |
| A22 | | 2-[[6-[[(2,3-Dihydro-5-benzofuranyl)methyl]amino]-7-ethyl-7H-purin-2-yl]amino]-4-methyl-5-thiazolecarboxylic acid ethyl ester | 1.57 | 480.13 |
| A23 | | 2-[[6-[[(3-Chloro-4-methylphenyl)methyl]amino]-7-ethyl-7H-purin-2-yl]amino]-4-methyl-5-thiazolecarboxylic acid ethyl ester | 1.78 | 486.10 |
| A24 | | 2-[[6-[[(3,5-Dimethylphenyl)methyl]amino]-7-ethyl-7H-purin-2-yl]amino]-4-methyl-5-thiazolecarboxylic acid ethyl ester | 1.78 | 466.15 |
| A25 | | 2-[[6-[(2,3-Dihydro-6-methoxy-1H-inden-1-yl)amino]-7-ethyl-7H-purin-2-yl]amino]-4-methyl-5-thiazolecarboxylic acid ethyl ester | 1.69 | 494.15 |
| A26 | | 2-[[6-[(2,3-Dihydro-5-methoxy-1H-inden-1-yl)amino]-7-ethyl-7H-purin-2-yl]amino]-4-methyl-5-thiazolecarboxylic acid ethyl ester | 1.70 | 494.15 |

TABLE A-continued

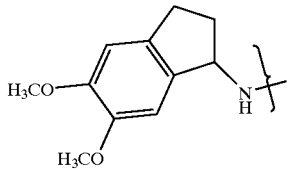

| Ex# | Z | Name | HPLC Retention | MS Reported |
|---|---|---|---|---|
| A27 | 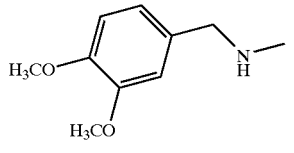 | 2-[[6-[(2,3-Dihydro-5,6-dimethoxy-1H-inden-1-yl)amino]-7-ethyl-7H-purin-2-yl]amino]-4-methyl-5-thiazolecarboxylic acid ethyl ester | 1.61 | 524.14 |
| A28 | 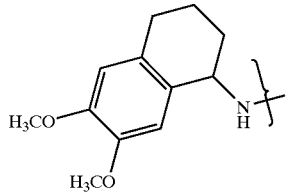 | 2-[[6-[[(3,4-Dimethoxyphenyl)methyl]amino]-7-ethyl-7H-purin-2-yl]amino]-4-methyl-5-thiazolecarboxylic acid ethyl ester | 1.54 | 532.2 |
| A29 | 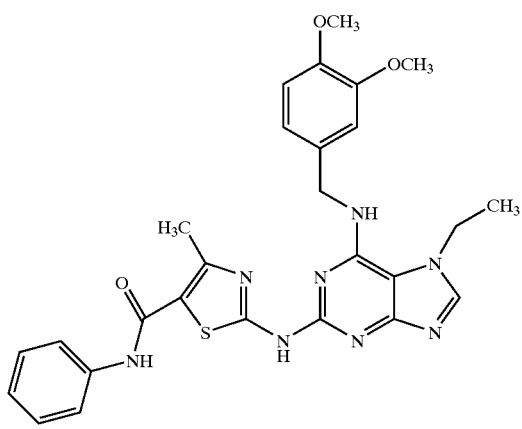 | 2-[[7-Ethyl-6-[(1,2,3,4-tetrahydro-6,7-dimethoxy-1-naphthalenyl)amino]-7H-purin-2-yl]amino]-4-methyl-5-thiazolecarboxylic acid ethyl ester | 1.66 | 538.14 |

Example A30

2-[[6-[[[4-(3,4-Dimethoxyphenyl)methyl]amino]-7-ethyl-7H-purin-2-yl]amino]-4-methyl-N-phenyl-5-thiazolecarboxamide

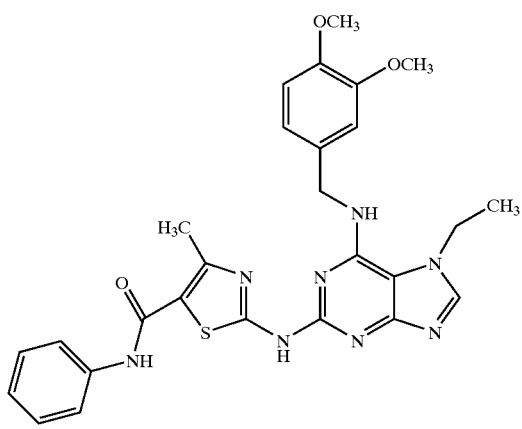

To Example A28 (100 mg, 0.20 mmol, 1 eq.) in a 2 dram vial with a teflon-lined cap, was added EtOH (2 ml) and concentrated NaOH (18M, 0.1 ml, 10 eq.). The vial was capped and heated at 70° C. for 48 hours. The reaction was cooled and acidified with concentrated HCl, the solution was then concentrated in vacuo to the crude mixture. The crude product mixture was purified by Prep HPLC (30% Solvent B, 10 minutes gradient) to give pure 2-[[6-[[[4-(3,4-Dimethoxyphenyl)methyl]amino]-7-ethyl-7H-purin-2-yl]amino]-4-methyl-N-(phenylmethyl)-5-thiazolecarboxylic acid. This acid (15.2 mg, 0.032 mmol, 1.0 eq.) in a 2 dram vial was added DMF (2 ml), 1,3-diisopropyl carbodimide (DIC) (12.3 mg, 0.097 mmol, 3 eq.), 1-hydroxy-7-azabenzotriazole (HOAt)(13.2 mg, 0.097 mmol, 3 eq.) and aniline (10.5 mg, 0.097 mmol, 3 eq.). The reaction solution was stirred at room temperature for 2 days. The crude product mixture was loaded onto a SCX cartridge. The cartridge was washed with methanol (3×5 ml) and the washing were discarded. The cartridge was eluted with ammonia in methanol (2M) (5 ml) and the eluent was collected and concentrated in vacuo to provide the desired product which was still contaminated. The product mixture was further purified by Prep HPLC (30% Solvent B, 5 minutes gradient) to give Example A30.

Example B1–B7

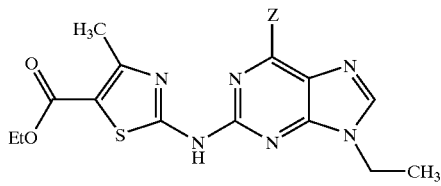

Examples B1 to B7 were prepared using N-9-ethyl-2,6-dichloropurine and general method A1.2 as outlined in for the preparation of purines in solution with the following exceptions. In step A1.2a, amines, alcohols, thiols, and sulfonamides, were used as the nucleophile. In step A1.2b S-Tol-BINAP was replaced with 2-(di-t-butylphosphino)biphenyl, and sodium tert-butoxide was replaced with anhydrous tribasic potassium phosphate and the solvent mixture of toluene (1.5 ml) and dioxane (1.5 ml), was replaced with DMA.

TABLE B

| Ex# | R | Name | HPLC[1] Retention | MS Reported |
|---|---|---|---|---|
| B1 | | 2-[[6(3,4-Dihydro-6,7-dimethoxy-2(1H)-isoquinolinyl)-9-ethyl-9H-purin-2-yl]amino]-4-methyl-5-thiazolecarboxylic acid ethyl ester | 3.93 | 524.44 |
| B2 | | 2-[[6-[[[4-(Aminosulfonyl)phenyl]methyl]amino]-9-ethyl-9H-purin-2-yl]amino]-4-methyl-5-thiazolecarboxilic acid ethyl ester | 3.15 | 517.04 |
| B3 | | 2-[[6-[[(4-Carboxyphenyl)methyl]amino]-9-ethyl-9H-purin-2-yl]amino]-4-methyl-5-thiazolecarboxilic acid ethyl ester | 3.48 | 482.13 |
| B4 | | 2-[[9-ethyl-6-[[(4-methoxyphenyl)methyl]thio]-9H-purin-2-yl]amino]-4-methyl-5-thiazolecarboxylic acid ethyl ester | 4.0 | 485.06 |
| B5 | | 2-[[9-Ethyl-6-[[4-(methylsulfonyl)phenyl]methoxy]-9H-purin-2-yl]amino]-4-methyl-5-thiazolecarboxylic acid ethyl ester | 3.48 | 517.12 |
| B6 | | 2-[[9-Ethyl-6-[[4-(methylsulfinyl)phenyl]methoxy]-9H-purin-2-yl]amino]-4-methyl-5-thiazolecarboxylic acid ethyl ester | 3.46 | 501.13 |

TABLE B-continued

| Ex# | R | Name | HPLC[1] Retention | MS Reported |
|---|---|---|---|---|
| B7 | H₃C-S(=O)(=O)-C₆H₄-S(=O)(=O)-N(H)- | 2-[[9-Ethyl-6-[[[4-(methylsulfonyl)phenyl]sulfonyl]amino]-9H-purin-2-yl]amino]-4-methyl-5-thiazolecarboxylic acid, ethyl ester. | 3.19 | 566.02 |
| B8 | 3,4-(MeO)₂-C₆H₃-CH₂-N(H)- | 2-[[6-[[(3,4-Dimethoxyphenyl)methyl]amino]-9-ethyl-9H-purin-2-]amino]-4-methyl-5-thiazolecarboxylic acid, ethyl ester, trifluoroacetate (1:1) | 3.59 | 498.13 |

[1]HPLC conditions used to determine retention times; 4 min gradient 0–100% B in A(A; 0.1% TFA in 90/10 water/methanol; B; 0.1% TFA in 10/90 water/methanol) using a YMC S5 C18 column at 220 nm.

Example C1

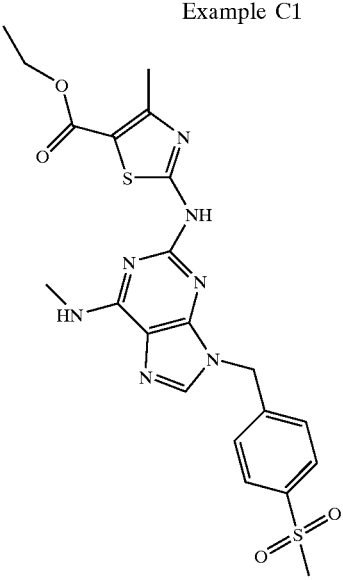

4-Methyl-2-[[6-(methylamino)-9-[[4-(methylsulfonyl)phenyl]methyl]-9H-purin-2-yl]amino]-5-thiazolecarboxylic acid ethyl ester

C1.1: 2.6-Dichloro-9-(4-methylsulfonylbenzyl)purine

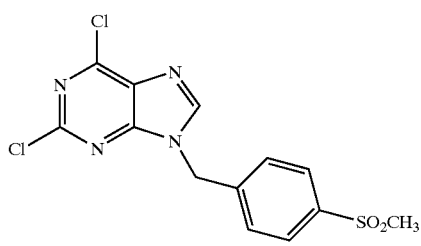

Potassium carbonate (823 mg, 5.95 mmol, 4.5 eq) was added to a solution of 2,6-dichloropuprine (250 mg, 1.32 mmol, 1 eq) in N,N-dimethylformamide (13 mL) and the resultant mixture was stirred at rt for 20 min before 4-methylsulfonylbenzyl chloride (541 mg, 2.64 mmol, 2 eq) was added. After stirring for 46 h at rt, the reaction mixture was filtered and the filtrate was concentrated in vacuo and purified by column chromatography [acetone/ethyl acetate/hexanes=1:1:2 (v/v)] to afford 304 mg (64%) of C1.1, as a white solid. LC/MS: 358 [M+H]⁺; HPLC: >99% at 2.94 min (PHENOMENEX 5 μm C18 column 4.6×50 mm, 10–90% aqueous methanol over 4 min containing 0.2% phosphoric acid, 4 mL/min, monitoring at 254 nm); ¹H NMR (400 MHz, DMSO-d₆): δ 8.87 (s, 1 H), 7.91 (d, J=8.3 Hz, 2 H), 7.57 (d, J=8.3 Hz, 2 H), 5.64 (s, 2 H), 3.20 (s, 3 H).

C1.2: 2-Chloro-6-(N-methylamino)-9-(4-methylsulfonylbenzyl)purine

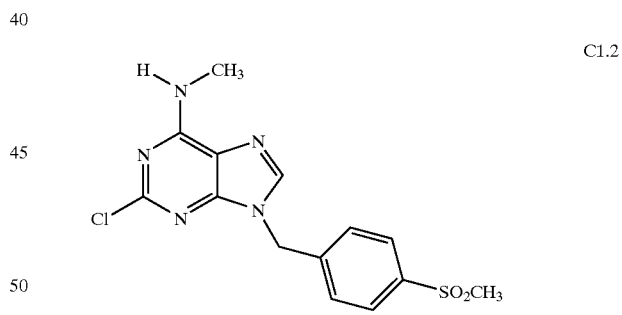

A mixture of 2,6-dichloro-9-(4-methylsulfonylbenzyl)purine (30 mg, 0.084 mmol, 1 eq), methylamine (8.03 M in ethanol, 21 μL, 0.168 mmol, 2 eq), and diisopropylethylamine (50 μL, 0.277 mmol, 3.3 eq) in 1-butanol (0.85 mL) was heated at 100° C. for 3 h. The reaction mixture was cooled to rt and the solid was collected by filtration, washed with cold methanol and dried to provide 22 mg (75%) of C1.2 as a slightly yellow solid. LC/MS: 352 [M+H]⁺; HPLC: >90% at 2.72 thin (PHENOMENEX 5 μm C18 column 4.6×50 mm, 10–90% aqueous methanol over 4 min containing 0.2% phosphoric acid, 4 mL/min, monitoring at 254 nm); ¹H NMR (400 MHz, DMSO-d₆): δ 8.31 (br s, 1 H), 8.29 (s, 1 H), 7.91 (d, J=8.3 Hz, 2 H), 7.48 (d, J=8.2 Hz, 2 H), 5.48 (s, 2 H), 3.19 (s, 3 H), 2.92 (d, J=4.3 Hz, 3 H).

47

C1.3: 4-Methyl-2-[[6-(methylamino)-9-[[4-(methylsulfonyl)phenyl]methyl]-9H-purin-2-yl]amino]-5-thiazolecarboxylic acid ethyl ester

To a solution of C1.2 (35.6 mg, 0.101 mmol, 1 eq) and ethyl 2-amino4-methylthiazole-5-carboxylate (37.7 mg, 0.202 mmol, 2 eq) in dimethylacetamide (1 mL) in a 1-dram vial was added tris(dibenzylideneacetone)dipalladium(0) (9.2 mg, 0.010 mmol, 0.1 eq), 2-di-t-butylphosphino) biphenyl (9.0 mg, 0.030 mmol, 0.3 eq) and sodium t-butoxide (19.4 mg, 0.202 mmol, 2 eq). The vial was purged with $N_2$, sealed and heated in a 105° C. oil bath for 5 h. The reaction mixture was cooled to rt, filtered through celite and concentrated in vacuo. The residue was treated with methanol (ca. 1 mL) and the precipitated solid was collected by filtration, washed with methanol and dried to afford 30 mg (60%) of product as a tan solid. LC/MS: 502 $[M+H]^+$; HPLC: >90% at 3.52 min (PHENOMENEX 5 $\mu$m C18 column 4.6×50 mm, 10–90% aqueous methanol over 4 min containing 0.2% phosphoric acid, 4 mL/min, monitoring at 254 nm); $^1$H NMR (400 MHz, DMSO-$d_6$): δ 11.55 (s, 1 H), 8.16 (s, 1 H), 8.00 (br s, 1 H), 7.89 (d, J=8.3 Hz, 2 H), 7.56 (d, J=8.0 Hz, 2 H), 5.47 (s, 2 H), 4.22 (q, J=7.0 Hz, 2 H), 3.16 (s, 3 H), 3.05 (br s, 3 H), 1.28 (t, J=7.0 Hz, 3 H).

48

Example C2–C22

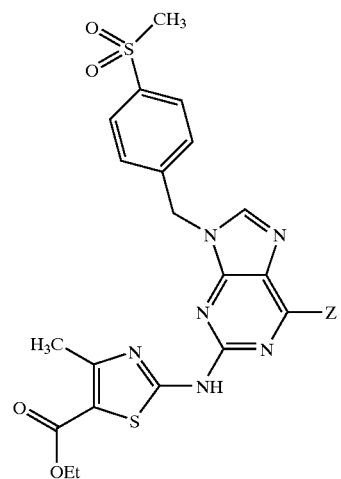

Examples C2 to C22 were prepared in a similar manner to that used for Example C1 with the exception that the appropriate amine was used in step C1.2. In the case of Example C4 was prepared from examples C3 by removal of the t-butyl group by treatment with trifluoroacetic acid.

TABLE C

| Ex# | Z | Name | HPLC[1] Retention | MS Reported |
|---|---|---|---|---|
| C2 | 4-(methylsulfonyl)phenyl-CH2-NH- | 4-Methyl-2-[[9-[[4-(methylsulfonyl)phenyl]methyl]-6-[[[4-(methylsulfonyl)phenyl]methyl]amino]-9H-purin-2-yl]amino]-5-thiazolecarboxylic acid ethyl ester | 3.20 | 656.12 |
| C3 | BOC-piperazinyl | 4-Methyl-2-[[9-[[4-(methylsulfonyl)phenyl]methyl]-6-(4-tert-butyloxycarbonyl-1-piperazinyl)-9H-purin-2-yl]amino]-5-thiazolecarboxylic acid ethyl ester | 3.76 | 657.04 |
| C4 | piperazinyl | 4-Methyl-2-[[9-[[4-(methylsulfonyl)phenyl]methyl]-6-(1-piperazinyl)-9H-purin-2-yl]amino]-5-thiazolecarboxylic acid ethyl ester | 2.84 | 557.10 |
| C5 | (CH3)2N-CH2CH2-N- | 2-[[6-[[2-(Dimethylamino)ethyl]amino]-9-[[4-(methylsulfonyl)phenyl]methyl]-9H-purin-2-yl]amino]-4-methyl-5-thiazolecarboxylic acid ethyl ester | 2.55 | 559.47 |
| C6 | morpholinyl | 4-Methyl-2-[[9-[[4-(methylsulfonyl)phenyl]methyl]-6-(4-morpholinyl)-9H-purin-2-yl]amino]-5-thiazolecarboxylic acid ethyl ester | 3.24 | 558.26 |
| C7 | 3-pyridinylmethyl-NH- | 4-Methyl-2-[[9-[[4-(methylsulfonyl)phenyl]methyl]-6-[(3-pyridinylmethyl)amino]-9H-purin-2-yl]amino]-5-thiazolecarboxylic acid ethyl ester | 2.60 | 579.44 |

TABLE C-continued

| Ex# | Z | Name | HPLC[1] Retention | MS Reported |
|---|---|---|---|---|
| C8 | 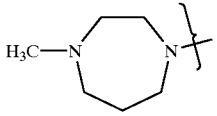 | 2-[[6-[(Hexahydro-4-methyl-1H-1,4-diazepin-1-yl)amino]-9-[[4-(methylsulfonyl)phenyl]methyl]-9H-purin-2-yl]amino]-4-methyl-5-thiazolecarboxylic acid ethyl ester | 2.65 | 585.45 |
| C9 | 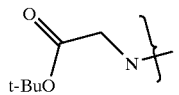 | 2-[[6-[[2-(1,1-Dimethylethoxy)-2-oxoethyl]amino]-9-[[4-(methylsulfonyl)phenyl]methyl]-9H-purin-2-yl]amino]-4-methyl-5-thiazolecarboxylic acid ethyl ester | 3.33 | 602.36 |
| C10 | 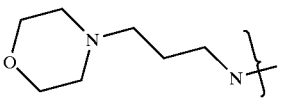 | 4-Methyl-2-[[9-[[4-(methylsulfonyl)phenyl]methyl]-6-[[3-(4-morpholinyl)propyl]amino]-9H-purin-2-yl]amino]-5-thiazolecarboxylic acid ethyl ester | 2.60 | 6.15.45 |
| C11 | 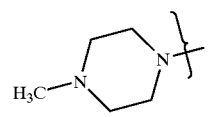 | 4-Methyl-2-[[6-(4-methyl-1-piperazinyl)-9-[[4-(methylsulfonyl)phenyl]methyl]-9H-purin-2-yl]amino]-5-thiazolecarboxylic acid ethyl ester | 2.57 | 571.43 |
| C12 | 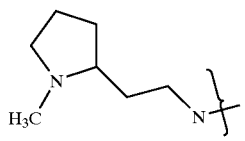 | 4-Methyl-2-[[6-[[2-(1-methyl-2-pyrrolidinyl)ethyl]amino]-9-[[4-(methylsulfonyl)phenyl]methyl]-9H-purin-2-yl]amino]-5-thiazolecarboxylic acid ethyl ester | 2.66 | 599.43 |
| C13 | 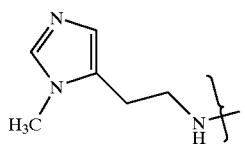 | 4-Methyl-2-[[6-[[2-(1-methyl-1H-imidazol-5-yl)ethyl]amino]-9-[[4-(methylsulfonyl)phenyl]methyl]-9H-purin-2-yl]amino]-5-thiazolecarboxylic acid ethyl ester | 2.62 | 596.42 |
| C14 | 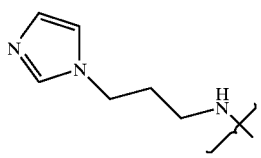 | 2-[[6-[[3-(1H-Imidazol-1-yl)propyl]amino]-9-[[4-(methylsulfonyl)phenyl]methyl]-9H-purin-2-yl]amino]-4-methyl-5-thiazolecarboxylic acid ethyl ester | 2.66 | 596.41 |
| C15 | 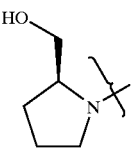 | 2-[[6-[(2S)-2-(Hydroxymethyl)-1-pyrrolidinyl]-9-[[4-(methylsulfonyl)phenyl]methyl]-9H-purin-2-yl]amino]-4-methyl-5-thiazolecarboxylic acid ethyl ester | 3.04 | 572.16 |
| C16 | 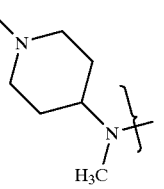 | 4-Methyl-2-[[6-[methyl(1-methyl-4-piperidinyl)amino]-9-[[4-(methylsulfonyl)phenyl]methyl]-9H-purin-2-yl]amino]-5-thiazolecarboxylic acid ethyl ester | 2.75 | 599.19 |
| C17 | 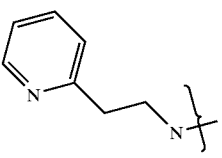 | 4-Methyl-2-[[9-[[4-(methylsulfonyl)phenyl]methyl]-6-[[2-(2-pyridinyl)ethyl]amino]-9H-purin-2-yl]amino]-5-thiazolecarboxylic acid ethyl ester | 2.67 | 593.35 |

TABLE C-continued

| Ex# | Z | Name | HPLC[1] Retention | MS Reported |
|---|---|---|---|---|
| C18 | (2-pyridinylmethyl)amino | 4-Methyl-2-[[9-[[4-(methylsulfonyl)phenyl]methyl]-6-[(2-pyridinylmethyl)amino]-9H-purin-2-yl]amino]-5-thiazolecarboxylic acid ethyl ester | 2.56 | 579.30 |
| C19 | (4-pyridinylmethyl)amino | 4-Methyl-2-[[9-[[4-(methylsulfonyl)phenyl]methyl]-6-[(4-pyridinylmethyl)amino]-9H-purin-2-yl]amino]-5-thiazolecarboxylic acid ethyl ester | 2.60 | 579.28 |
| C20 | 3-(hydroxymethyl)piperidinyl | 2-[[6-[3-(Hydroxymethyl)-1-piperidinyl]-9-[[4-(methylsulfonyl)phenyl]methyl]-9H-purin-2-yl]amino]-4-methyl-5-thiazolecarboxylic acid ethyl ester | 2.60 | 436.31 |
| C21 | dimethylamino | 2-[[6-(Dimethylamino)-9-[[4-(methylsulfonyl)phenyl]methyl]-9H-purin-2-yl]amino]-4-methyl-5-thiazolecarboxylic acid ethyl ester | 3.07 | 516.15 |
| C22 | (2-methoxyethyl)amino | 2-[[6-[(2-Methoxyethyl)amino]-9-[[4-(methylsulfonyl)phenyl]methyl]-9H-purin-2-yl]amino]-4-methyl-5-thiazolecarboxylic acid ethyl ester | 1.40[2] | 546.31 |

[1]HPLC conditions used to determine retention times; 4 min gradient 0–100% B in A(A; 0.1% TFA in 90/10 water/methanol; B; 0.1% TFA in 10/90 water/methanol) using a YMC S5 C18 column at 220 nm.
[2]HPLC conditions used to determine retention times; 2 min gradient 0–100% B in A(A; 0.1% TFA in 90/10 water/methanol; B; 0.1% TFA in 10/90 water/methanol) using a YMC S73 ODS column at 254 nm

Example D1

2-[[9-[(3,4-Dimethoxyphenyl)methyl]-6-(4-morpholinyl)-9H-purin-2-yl]amino]-4-methyl-5-thiazolecarboxylic acid, ethyl ester

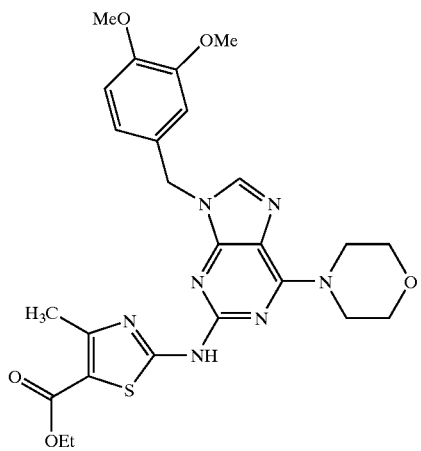

D1

Example D1 was prepared in a manner analogous to Example C1 with the exceptions that in step C1.1, 4-methylsulfonylbenzyl chloride was substituted with 3,4-dimethoxybenzyl chloride, and in step C1.2, methylamine was replaced with morpholine. Step C1.3 was conducted in an almost identical manner substituting the appropriate monochloropurine. LCMS: Ret. Time=3.59 min. M+=498.13. HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm

Example D2

2-[[9-[(pyridin-3-yl)methyl]-6-(4-morpholinyl)-9H-purin-2-yl]amino]-4-methyl-5-thiazolecarboxylic acid, ethyl ester

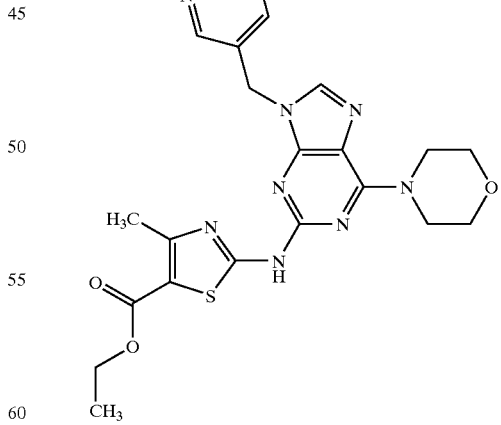

D2

Example D2 was prepared in a manner analogous to Example C1 with the exceptions that in step C1.1 4-methylsulfonylbenzyl chloride was substituted for 3-picolylchloride hydrochloride. LCMS: retention time= 1.54 min, M+=480.00. HPLC conditions used to determine retention times; 2 min gradient 0–100% B in A(A; 0.1% TFA in 90/10 water/methanol; B; 0.1% TFA in 10/90 water/methanol) using a PHENOMENEX column at 220 nm detection.

Example D3

N-[4-(5-Methyl-2-pyrimidinyl)phenyl]-6-(4-morpholinyl)-9-(2-pyridinylmethyl)-9H-purin-2-amine

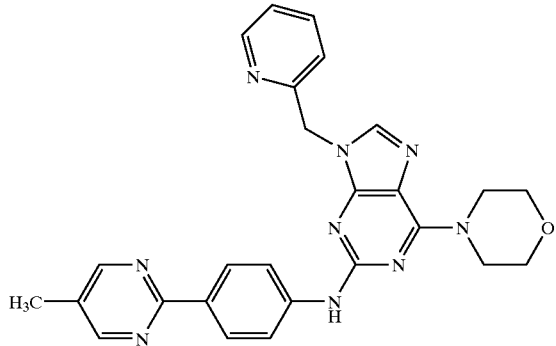

D3

Example D3 was prepared in a manner analogous to Example C1 with the exceptions that in step C1.1, 4-methylsulfonylbenzyl chloride was substituted with 2-picolylchloride hydrochloride, and in step C1.2, methylamine was replaced with morpholine. Step C1.3 was conducted in an almost identical manner substituting D3.1, 4-(4-methylpyrimidn-2-yl)aniline for ethyl-2-amino-4-methylthiazole-5-carboxylate. LCMS: retention time=1.51 min, M+=479.00. HPLC conditions used to determine retention times; 2 min gradient 0–100% B in A(A; 0.1% TFA in 90/10 water/methanol; B; 0.1% TFA in 10/90 water/methanol) using a PHENOMENEX column at 220 nm detection.

D3.1: 4-(4-methylpyrimidin-2-yl)aniline for ethyl-2-amino-4-methylthiazole-5-carboxylate

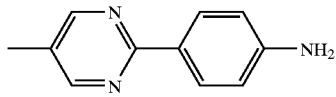

D3.1

4Aminobenzamidine dihydrochloride (2.1 g, 0.01 mmol), and 3-ethoxymethacreolein (1.2 g, 0.010 mmol) were dissolved in methanol at room temperature. 25% Sodium methoxide (4.3 g, 0.020 mmol) was added and the reaction mixture stirred for 1.5 h. The solvent was evaporated under reduced pressure, and the resulting oil partitioned between water and ether. The organic layer was dried with magnesium sulfate, filtered and evaporated to provide 1.2 g (65% yield) D3.1 as a solid. MS (M+H)$^+$=185.

We claim:
1. A compound selected from
(i)

2-[[6-[(1,3-Benzodioxol-5-ylmethyl)amino]-7-ethyl-7H-purin-2-yl]amino]-4-methyl-5-thiazolecarboxylic acid ethyl ester;
2-[[7-Ethyl-6-[(3-pyridinylmethyl)amino]-7H-purin-2-yl]amino]-4-methyl-5-thiazolecarboxylic acid ethyl ester;
2-[[7-Ethyl-6-[[(3,4,5-trimethoxyphenyl)methyl]amino]-7H-purin-2-yl]amino]-4-methyl-5-thiazolecarboxylic acid ethyl ester;
2-[[7-Ethyl-6-[[[4-(methylsulfonyl)phenyl]methyl]amino]-7H-purin-2-yl]amino]-4-methyl-5-thiazolecarboxylic acid ethyl ester;
4-Methyl-2-[[6-[[(1R)-1-phenylethyl]amino]-7-ethyl-7H-purin-2-yl]amino]-5-thiazolecarboxylic acid ethyl ester;
4-Methyl-2-[[6-[[(1S)-1-phenylethyl]amino]-7-ethyl-7H-purin-2-yl]amino]-5-thiazolecarboxylic acid ethyl ester;
2-[[7-Ethyl-6-[(1,2,3,4-tetrahydro-1-naphthalenyl)amino]-7H-purin-2-yl]amino]-4-methyl-5-thiazolecarboxylic acid ethyl ester;
2-[[7-Ethyl-6-(1,2,3,4-tetrahydro-6,7-dimethoxy-2-isoquinolinyl)-7H-purin-2-yl]amino]-4-methyl-5-thiazolecarboxylic acid ethyl ester;
2-[[6-[[(1R)-2,3-Dihydro-1H-inden-1-yl]amino]-7-ethyl-7H-purin-2-yl]amino]-4-methyl-5-thiazolecarboxylic acid ethyl ester;
-[[6-[[(1S)-2,3-Dihydro-1H-inden-1-yl]amino]-7-ethyl-7H-purin-2-yl]amino]-4-methyl-5-thiazolecarboxylic acid ethyl ester;
2-[[6-[[[4-(Aminosulfonyl)phenyl]methyl]amino]-7-ethyl-7H-purin-2-yl]amino]-4-methyl-5-thiazolecarboxylic acid ethyl ester;
2-[[7-Ethyl-6-[[(2,3,4-trimethoxyphenyl)methyl]amino]-7H-purin-2-yl]amino]-4-methyl-5-thiazolecarboxylic acid ethyl ester;
2-[[7-Ethyl-6-[[[3-methoxy-4-(phenylmethoxy)phenyl]methyl]amino]-7H-purin-2-yl]amino]-4-methyl-5-thiazolecarboxylic acid ethyl ester;
2-[[7-Ethyl-6-[[(4-methoxy-3-methylphenyl)methyl]amino]-7H-purin-2-yl]amino]-4-methyl-5-thiazolecarboxylic acid ethyl ester;
2-[[6-[[(4-Cyanophenyl)methyl]amino]-7-ethyl-7H-purin-2-yl]amino]-4-methyl-5-thiazolecarboxylic acid ethyl ester;
2-[[6-[[[4-(Acetylamino)phenyl]methyl]amino]-7-ethyl-7H-purin-2-yl]amino]-4-methyl-5-thiazolecarboxylic acid ethyl ester;
2-[[7-Ethyl-6-[(3-quinolinylmethyl)amino]-7H-purin-2-yl]amino]-4-methyl-5-thiazolecarboxylic acid ethyl ester;
2-[[7-Ethyl-6-[[[4-(methylthio)phenyl]methyl]amino]-7H-purin-2-yl]amino]-4-methyl-5-thiazolecarboxylic acid ethyl ester;
2-[[7-Ethyl-6-[[[4-(methoxycarbonyl)phenyl]methyl]amino]-7H-purin-2-yl]amino]-4-methyl-5-thiazolecarboxylic acid ethyl ester;
2-[[7-Ethyl-6-[[(7-methoxy-1,3-benzodioxol-5-yl)methyl]amino]-7H-purin-2-yl]amino]-4-methyl-5-thiazolecarboxylic acid ethyl ester;
2-[[6-[(1,3-Benzodioxol-4-yl)methyl]amino]-7-ethyl-7H-purin-2-yl]amino]-4-methyl-5-thiazolecarboxylic acid ethyl ester;
2-[[6-[[(2,3-Dihydro-5-benzofuranyl)methyl]amino]-7-ethyl-7H-purin-2-yl]amino]-4-methyl-5-thiazolecarboxylic acid ethyl ester;
2-[[6-[[(3-Chloro-4-methylphenyl)methyl]amino]-7-ethyl-7H-purin-2-yl]amino]-4-methyl-5-thiazolecarboxylic acid ethyl ester;
2-[[6-[[(3,5-Dimethylphenyl)methyl]amino]-7-ethyl-7H-purin-2-yl]amino]-4-methyl-5-thiazolecarboxylic acid ethyl ester;
2-[[6-[(2,3-Dihydro-6-methoxy-1H-inden-1-yl)amino]-7-ethyl-7H-purin-2-yl]amino]-4-methyl-5-thiazolecarboxylic acid ethyl ester;
2-[[6-[(2,3-Dihydro-5-methoxy-1H-inden-1-yl)amino]-7-ethyl-7H-purin-2-yl]amino]-4-methyl-5-thiazolecarboxylic acid ethyl ester;

2-[[6-[(2,3-Dihydro-5,6-dimethoxy-1H-inden-1-yl)amino]-7-ethyl-7H-purin-2-yl]amino]-4-methyl-5-thiazolecarboxylic acid ethyl ester;

2-[[6-[[(3,4-Dimethoxyphenyl)methyl]amino]-7-ethyl-7H-purin-2-yl]amino]-4-methyl-5-thiazolecarboxylic acid ethyl ester;

2-[[7-Ethyl-6-[(1,2,3,4-tetrahydro-6,7-dimethoxy-1-naphthalenyl)amino]-7H-purin-2-yl]amino]-4-methyl-5-thiazolecarboxylic acid ethyl ester;

2-[[6-[[[4-(3,4-Dimethoxyphenyl)methyl]amino]-7-ethyl-7H-purin-2-yl]amino]-4-methyl-N-phenyl-5-thiazolecarboxamide;

2-[[6-(3,4-Dihydro-6,7-dimethoxy-2(1H)-isoquinolinyl)-9-ethyl-9H-purin-2-yl]amino]-4-methyl-5-thiazolecarboxylic acid ethyl ester;

2-[[6-[[[4-(Aminosulfonyl)phenyl]methyl]amino]-9-ethyl-9H-purin-2-yl]amino]-4-methyl-5-thiazolecarboxylic acid ethyl ester;

2-[[6-[[(4-Carboxyphenyl)methyl]amino]-9-ethyl-9H-purin-2-yl]amino]-4-methyl-5-thiazolecarboxylic acid ethyl ester;

2-[[9-Ethyl-6-[[(4-methoxyphenyl)methyl]thio]-9H-purin-2-yl]amino]-4-methyl-5-thiazolecarboxylic acid ethyl ester;

2-[[9-Ethyl-6-[[4-(methylsulfonyl)phenyl]methoxy]-9H-purin-2-yl]amino]-4-methyl-5-thiazolecarboxylic acid ethyl ester;

2-[[9-Ethyl-6-[[4-(methylsulfinyl)phenyl]methoxy]-9H-purin-2-yl]amino]-4-methyl-5-thiazolecarboxylic acid ethyl ester;

2-[[9-Ethyl-6-[[[4-(methylsulfonyl)phenyl]sulfonyl]amino]-9H-purin-2-yl]amino]-4-methyl-5-thiazolecarboxylic acid, ethyl ester;

2-[[6-[[(3,4-Dimethoxyphenyl)methyl]amino]-9-ethyl-9H-purin-2-yl]amino]-4-methyl-5-thiazolecarboxylic acid, ethyl ester, trifluoroacetate (1:1);

4-Methyl-2-[[6-(methylamino)-9-[[4-(methylsulfonyl)phenyl]methyl]-9H-purin-2-yl]amino]-5-thiazolecarboxylic acid ethyl ester;

4-Methyl-2-[[9-[[4-(methylsulfonyl)phenyl]methyl]-6-[[[4-(methylsulfonyl)phenyl]methyl]amino]-9H-purin-2-yl]amino]-5-thiazolecarboxylic acid ethyl ester;

4-Methyl-2-[[9-[[4-(methylsulfonyl)phenyl]methyl]-6-(4-tert-butyloxycarbonyl-1-piperazinyl)-9H-purin-2-yl]amino]-5-thiazolecarboxylic acid ethyl ester;

4-Methyl-2-[[9-[[4-(methylsulfonyl)phenyl]methyl]-6-(1-piperazinyl)-9H-purin-2-yl]amino]-5-thiazolecarboxylic acid ethyl ester;

2-[[6-[[2-(Dimethylamino)ethyl]amino]-9-[[4-(methylsulfonyl)phenyl]methyl]-9H-purin-2-yl]amino]-4-methyl-5-thiazolecarboxylic acid ethyl ester;

4-Methyl-2-[[9-[[4-(methylsulfonyl)phenyl]methyl]-6-(4-morpholinyl)-9H-purin-2-yl]amino]-5-thiazolecarboxylic acid ethyl ester;

4-Methyl-2-[[9-[[4-(methylsulfonyl)phenyl]methyl]-6-[(3-pyridinylmethyl)amino]-9H-purin-2-yl]amino]-5-thiazolecarboxylic acid ethyl ester;

2-[[6-[(Hexahydro-4-methyl-1H-1,4-diazepin-1-yl)amino]-9-[[4-(methylsulfonyl)phenyl]methyl]-9H-purin-2-yl]amino]-4-methyl-5-thiazolecarboxylic acid ethyl ester;

2-[[6-[[2-(1,1-Dimethylethoxy)-2-oxoethyl]amino]-9-[[4-(methylsulfonyl)phenyl]methyl]-9H-purin-2-yl]amino]-4-methyl-5-thiazolecarboxylic acid ethyl ester;

4-Methyl-2-[[9-[[4-(methylsulfonyl)phenyl]methyl]-6-[[3-(4-morpholinyl)propyl]amino]-9H-purin-2-yl]amino]-5-thiazolecarboxylic acid ethyl ester;

4-Methyl-2-[[6-(4-methyl-1-piperazinyl)-9-[[4-(methylsulfonyl)phenyl]methyl]-9H-purin-2-yl]amino]-5-thiazolecarboxylic acid ethyl ester;

4-Methyl-2-[[6-[[2-(1-methyl-2-pyrrolidinyl)ethyl]amino]-9-[[4-(methylsulfonyl)phenyl]methyl]-9H-purin-2-yl]amino]-5-thiazolecarboxylic acid ethyl ester;

4-Methyl-2-[[6-[[2-(1-methyl-1H-imidazol-5-yl)ethyl]amino]-9-[[4-(methylsulfonyl)phenyl]methyl]-9H-purin-2-yl]amino]-5-thiazolecarboxylic acid ethyl ester;

2-[[6-[[3-(1H-Imidazol-1-yl)propyl]amino]-9-[[4-(methylsulfonyl)phenyl]methyl]-9H-purin-2-yl]amino]-4-methyl-5-thiazolecarboxylic acid ethyl ester;

2-[[6-[(2S)-2-(Hydroxymethyl)-1-pyrrolidinyl]-9-[[4-(methylsulfonyl)phenyl]methyl]-9H-purin-2-yl]amino]-4-methyl-5-thiazolecarboxylic acid ethyl ester;

4-Methyl-2-[[6-[methyl(1-methyl-4-piperidinyl)amino]-9-[[4-(methylsulfonyl)phenyl]methyl]-9H-purin-2-yl]amino]-5-thiazolecarboxylic acid ethyl ester;

4-Methyl-2-[[9-[[4-(methylsulfonyl)phenyl]methyl]-6-[[2-(2-pyridinyl)ethyl]amino]-9H-purin-2-yl]amino]-5-thiazolecarboxylic acid ethyl ester;

4-Methyl-2-[[9-[[4-(methylsulfonyl)phenyl]methyl]-6-[(2-pyridinylmethyl)amino]-9H-purin-2-yl]amino]-5-thiazolecarboxylic acid ethyl ester;

4-Methyl-2-[[9-[[4-(methylsulfonyl)phenyl]methyl]-6-[(4-pyridinylmethyl)amino]-9H-purin-2-yl]amino]-5-thiazolecarboxylic acid ethyl ester;

2-[[6-[3-(Hydroxymethyl)-1-piperidinyl]-9-[[4-(methylsulfonyl)phenyl]methyl]-9H-purin-2-yl]amino]-4-methyl-5-thiazolecarboxylic acid ethyl est;

2-[[6-(Dimethylamino)-9-[[4-(methylsulfonyl)phenyl]methyl]-9H-purin-2-yl]amino]-4-methyl-5-thiazolecarboxylic acid ethyl ester;

2-[[6-[(2-Methoxyethyl)amino]-9-[[4-(methylsulfonyl)phenyl]methyl]-9H-purin-2-yl]amino]-4-methyl-5-thiazolecarboxylic acid ethyl ester;

2-[[9-[(3,4-Dimethoxyphenyl)methyl]-6-(4-morpholinyl)-9H-purin-2-yl]amino]-4-methyl-5-thiazolecarboxylic acid, ethyl ester;

2-[[9-[(pyridin-3-yl)methyl]-6-(4-morpholinyl)-9H-purin-2-yl]amino]-4-methyl-5-thiazolecarboxylic acid, ethyl ester; and N-[4-(5-Methyl-2-pyrimidinyl)phenyl]-6-(4-morpholinyl)-9-(2-pyridinylmethyl)-9H-purin-2-amine; or (ii) enantiomers, diastereomers and salts of (i) thereof.

* * * * *